US011147819B2

(12) United States Patent
Ribich et al.

(10) Patent No.: US 11,147,819 B2
(45) Date of Patent: Oct. 19, 2021

(54) EZH2 INHIBITORS FOR TREATING CANCER

(71) Applicant: Epizyme, Inc., Cambridge, MA (US)

(72) Inventors: Scott Ribich, Lexington, MA (US); Michael Thomenius, Rockland, MA (US)

(73) Assignee: Epizyme, Inc., Cambridge, MA (US)

( * ) Notice: Subject to any disclaimer, the term of this patent is extended or adjusted under 35 U.S.C. 154(b) by 381 days.

(21) Appl. No.: 16/310,597

(22) PCT Filed: Jun. 16, 2017

(86) PCT No.: PCT/US2017/037973
§ 371 (c)(1),
(2) Date: Dec. 17, 2018

(87) PCT Pub. No.: WO2017/218953
PCT Pub. Date: Dec. 21, 2017

(65) Prior Publication Data
US 2019/0328743 A1 Oct. 31, 2019

Related U.S. Application Data

(60) Provisional application No. 62/351,878, filed on Jun. 17, 2016.

(51) Int. Cl.
| | | |
|---|---|---|
| A61K 31/5375 | (2006.01) | |
| A61K 31/496 | (2006.01) | |
| A61P 35/00 | (2006.01) | |
| A61K 31/5377 | (2006.01) | |
| A61K 9/00 | (2006.01) | |
| A61K 45/06 | (2006.01) | |

(52) U.S. Cl.
CPC ........ *A61K 31/5377* (2013.01); *A61K 9/0053* (2013.01); *A61P 35/00* (2018.01); *A61K 45/06* (2013.01)

(58) Field of Classification Search
CPC ............ A61K 39/0011; A61K 31/5375; A61K 9/0053; A61K 31/496; A61P 35/00
USPC .................... 514/19.3, 233.5, 235.5, 252.13
See application file for complete search history.

(56) References Cited

U.S. PATENT DOCUMENTS

| | | | |
|---|---|---|---|
| 8,536,179 | B2 | 9/2013 | Miller et al. |
| 2003/0175736 | A1 | 9/2003 | Chinnaiyan et al. |
| 2012/0264734 | A1 | 10/2012 | Kuntz et al. |
| 2014/0107122 | A1 | 4/2014 | Kuntz et al. |
| 2015/0099747 | A1 | 4/2015 | Ma et al. |
| 2015/0141362 | A1 | 5/2015 | Copeland et al. |
| 2015/0232548 | A1 | 8/2015 | Klein et al. |
| 2015/0320779 | A1 | 11/2015 | Fillmore et al. |
| 2015/0368229 | A1 | 12/2015 | Albrecht et al. |
| 2020/0323866 | A1* | 10/2020 | Keilhack ................. A61P 35/00 |

FOREIGN PATENT DOCUMENTS

| | | |
|---|---|---|
| WO | WO 2011/140324 A1 | 11/2011 |
| WO | WO 2012/034132 A2 | 3/2012 |
| WO | WO 2012/118812 A2 | 9/2012 |
| WO | WO 2012/142504 A1 | 10/2012 |
| WO | WO 2012/142513 A1 | 10/2012 |
| WO | WO 2013/120104 A2 | 8/2013 |
| WO | WO 2013/138361 A1 | 9/2013 |
| WO | WO 2013/155317 A1 | 10/2013 |
| WO | WO 2013/155464 A1 | 10/2013 |
| WO | WO 2014/062720 A2 | 4/2014 |
| WO | WO 2014/062732 A1 | 4/2014 |
| WO | WO 2014/062733 A2 | 4/2014 |
| WO | WO 2014/100646 A1 | 6/2014 |
| WO | WO 2014/100665 A1 | 6/2014 |
| WO | WO 2014/124418 A1 | 8/2014 |
| WO | WO 2014/144747 A1 | 9/2014 |
| WO | WO 2014/172044 A1 | 10/2014 |
| WO | WO 2015/010049 A1 | 1/2015 |
| WO | WO 2015/010078 A2 | 1/2015 |
| WO | WO 2015/057859 A1 | 4/2015 |
| WO | WO 2015/058125 A1 | 4/2015 |
| WO | WO 2015/085325 A1 | 6/2015 |
| WO | WO 2015/195848 A1 | 12/2015 |
| WO | WO 2015/200650 A9 | 12/2015 |
| WO | WO 2016/061507 A1 | 4/2016 |
| WO | WO 2016/081523 A1 | 5/2016 |
| WO | WO 2016/172199 A1 | 10/2016 |
| WO | WO 2016/201328 A1 | 12/2016 |
| WO | WO 2017/019721 A2 | 2/2017 |

(Continued)

OTHER PUBLICATIONS

Advani, R.H. et al. (2006) "Sgn-40 (Anti-huCD40 mAb) Monotherapy Induces Durable Objective Responses in Patients with Relapsed Aggressive Non-Hodgkin's Lymphoma: Evidence of Antitumor Activity From a Phase 1 Study" *Blood*, 108(11):695 [online]. Retrieved from http://www.bloodjournal.org/content/108/11/695; retrieved Jul. 18, 2019, 2 printed pages.

Chan-Penebre, E. et al. (2017) "Selective Killing of SMARCA2- and SMARCA4-deficient Small Cell Carcinoma of the Ovary, Hypercalcemic Type Cells by Inhibition of EZH2: In Vitro and In Vivo Preclinical Models" *Mol Cancer Ther*, 16(5):850-860.

Chase, A. and N. C. Cross (2011) "Aberrations of EZH2 in cancer" *Clin Cancer Res*, 17(9):2613-2618.

Copeland, R. A. (2013) "Molecular pathways: protein methyltransferases in cancer" *Clin Cancer Res*, 19(23):6344-6350.

(Continued)

*Primary Examiner* — Raymond J Henley, III

(74) *Attorney, Agent, or Firm* — Cooley LLP; Heidi A. Erlacher; Christine C. Pemberton

(57) ABSTRACT

The present disclosure relates to compositions comprising inhibitors of human histone methyltransferase EZH2 and one or more other therapeutic agents, for example, modulators of CD40 pathway activity, such as CD40 agonists, and methods of combination therapy for administering to subjects in need thereof for the treatment of cancer.

29 Claims, 10 Drawing Sheets

(56) References Cited

FOREIGN PATENT DOCUMENTS

| WO | WO 2017/035234 A1 | 3/2017 |
|----|----|----|
| WO | WO 2017/053930 A2 | 3/2017 |
| WO | WO 2017/062495 A2 | 4/2017 |
| WO | WO 2017/079757 A1 | 5/2017 |
| WO | WO 2017/100362 A2 | 6/2017 |
| WO | WO 2017/132518 A1 | 8/2017 |
| WO | WO 2017/139404 A1 | 8/2017 |
| WO | WO 2017/210395 A1 | 12/2017 |

OTHER PUBLICATIONS

Fiskus et al. (2009) "Combined epigenetic therapy with the histone methyltransferase EZH2 inhibitor 3-deazaneplanocin A and the histone deacetylase inhibitor panobinostat against human AML cells" *Blood*, 114(13):2733-2743.

Garapaty-Rao, S. et al. (Nov. 2013) "Identification of EZH2 and EZH1 Small Molecule Inhibitors with Selective Impact on Diffuse Large B Cell Lymphoma Cell Growth" *Chem Biol*, 20:1329-1339.

Hornick, J.L. et al. (2009) "Loss of INI1 expression is characteristic of both conventional and proximal-type epithelioid sarcoma" *Am J Surg Pathol*, 33(4):542-550.

Kadoch, C. et al. (2016) "PRC2 and SWI/SNF Chromatin Remodeling Complexes in Health and Disease" *Biochemistry*, 55(11):1600-1614.

Kleer, C.G. et al. (2003) "EZH2 is a marker of aggressive breast cancer and promotes neoplastic transformation of breast epithelial cells" *Proc Natl Acad Sci USA*, 100(20):11606-11611.

Knutson, S.K. et al. (2012) "A Selective Inhibitor of EZH2 Blocks H3K27 Methylation and Kills Mutant Lymphoma Cells" *Nat Chem Biol*, 8:890-896.

Knutson, S.K. et al. (2013) "Durable tumor regression in genetically altered malignant rhabdoid tumors by inhibition of methyltransferase EZH2" *Proc Natl Acad Sci USA*, 110(19):7922-7927.

Knutson, S.K. et at (Apr. 2014) "Selective inhibition of EZH2 by EPZ-6438 leads to potent antitumor activity in EZH2-mutant non-Hodgkin lymphoma" *Mol Cancer Ther*, 13(4):842-854.

Knutson, S.K. et at (Dec. 10, 2014) "Synergistic antitumor activity of EZH2 inhibitors and glucocorticoid receptor agonists in models of germinal center non-Hodgkin lymphomas" *PLoS One*, 9(12):e111840, 22 pages.

Margueron, R. and D. Reinberg (2011) "The Polycomb complex PRC2 and its mark in life" *Nature*, 469(7330):343-349.

Qi, W. et al. (2012) "Selective inhibition of Ezh2 by a small molecule inhibitor blocks tumor cells proliferation" *Proc Natl Acad Sci USA*, 109(52):21360-21365.

Varambally, S. et al.(2002) "The Polycomb Group Protein EZH2 Is Involved in Progression of Prostate Cancer" Nature, 419:624-629.

Vonderheide, R.H. (2007) "Prospect of targeting the CD40 pathway for cancer therapy" *Clin Cancer Res*, 13(4):1083-1088.

Vonderheide, R.H. and M.J. Glennie (2013) "Agonistic CD40 antibodies and cancer therapy" *Clin Cancer Res*, 19(5):1035-1043.

Wilson, B.G. et al. (Oct. 2010) "Epigenetic Antagonism between Polycomb and SWI/SNF Complexes during Oncogenic Transformation" *Cancer Cell*, 18(4):316-328.

Lewis, T.S. et al. (Dec. 11, 2007) "The humanized anti-CD40 monoclonal antibody, SGN-40, potentiates chemotherapy regimens in NHL xenograft models via pro-apoptotic signaling" *Blood*, 110(11 pt. 1):2342.

* cited by examiner

FIGURE 8

| | | Mutant EZH2 GCB | | | | WT EZH2 GCB | | | | | WT EZH2 ABC | | |
|---|---|---|---|---|---|---|---|---|---|---|---|---|---|
| | Drug Name | WSU-DLCL2 | KARPAS-422 | ^SU-DHL-10 | SU-DHL-6 | OCI-LY19 | HT | #Farage | OCI-LY7 | SUDHL5 | Toledo | TMD8 | OCI-LY3 | SUDHL2 |
| | IC50 Taz 7d/14d | 100 nM /86 nM | 100 nM /18 nM | 50 nM /58 nM | 100 nM /47 nM | 1 μM /6.2 μM | 500 nM /140 nM | 1 μM /99 nM | 1.5 μM /1.4 μM | 3.8 μM /2.1 μM | >10 μM /7.6 μM | 5.5 μM /2.6 μM | 5.1 μM /820 nM | 1.3 μM /230 nM |
| GRAG | Prednisolone | | | | | | | | | | | | | |
| | Dexamethasone | | | | | | | | | | | | | |
| | Everolimus | | | | | | | | | | | | | |
| | Trametinib | | | | | | | | | | | | | |
| | MK-2206 | | | | | | | | | | | | | |
| B-cell Receptor Pathway | Ibrutinib | | | | | | | | | | | | | |
| | Idelalisib | | | | | | | | | | | | | |
| | Tamatinib | | | | | | | | | | | | | |
| | CD40L | | | | | | | | | | | | | |
| B-cell Activators | LPS | | | | | | | | | | | | | |
| | BAFF | | | | | | | | | | | | | |
| | APRIL | | | | | | | | | | | | | |
| | Anti-IgM/IgG | | | | | | | | | | | | | |

Synergy or Enhancement | Additivity* | No Effect* | Antagonistic | Not tested

* Additivity = when other agent has a single agent effect but causes no enhancement of 6438 effect
No Effect = when other agent has no single agent effect and causes no enhancement of 6438 effect
^ Tested in 4-day cotreatment model
Tested in a 10 or 11 day assay with 7 days pretreatment 3 days or 4 days cotreatment

EZH2 INHIBITORS FOR TREATING CANCER

RELATED APPLICATIONS

This application is a U.S. National Phase application, filed under 35 U.S.C. § 371, of International Application No. PCT/US2017/037973, filed on Jun. 16, 2017, which claims priority to, and the benefit of, U.S. Provisional Application No. 62/351,878, filed on Jun. 17, 2016, the entire contents of each of which are incorporated herein by reference in their entireties.

BACKGROUND

EZH2, a histone methyltransferase, has been associated with various kinds of cancers. Specifically, mutations and and/or overactivity of EZH2 are found in a range of cancers, such as lymphomas, leukemias and breast cancer. There is an ongoing need for new agents as EZH2 inhibitors for use in anticancer treatment.

SUMMARY

The instant disclosure is based on the findings that EZH2 inhibitors have the capability of selectively killing cancer cells, regardless of EZH2 mutational status, both in vitro and in vivo. Additionally, EZH2 inhibitors are capable of working additively or synergistically when administered with second therapeutic agents.

In one aspect, the present disclosure provides methods for the treatment or prevention of cancer in a subject in need thereof. In some embodiments, the method includes administration of a therapeutically effective amount of an EZH2 inhibitor and of a second therapeutic agent to said subject.

The method can include one or more of the following features.

In some embodiments, the second therapeutic agent comprises an agent that shows synergy or an additive effect with tazemetostat in TABLE 1. In some embodiments, the second therapeutic agent is a CD40 agonist. In some embodiments, the CD40 agonist comprises CD40L, or a CD40-binding fragment of CD40L, an agonistic CD40 antibody or an agonistic CD40 antibody fragment, e.g., as described in Vonderheide et al., Clin. Cancer Res. 2013 Mar. 1; 19(5): 1035-43, *Agonistic* CD40 *antibodies and cancer therapy* (the entire contents of which are incorporated herein by reference), CP870,893 (Pfizer, Vonderheide R H. *Prospect of targeting the CD40 pathway for cancer therapy.* Clin Cancer Res. 2007; 13(4):1083-8 (the entire contents of which are incorporated herein by reference)), SGN-40 (Advani et al., *SGN-40 (anti-huCD40 mAb) monotherapy induces durable objective responses in patients with relapsed aggressive non-Hodgkin's lymphoma: evidence of anti-tumor activity from a phase* 1 *study.* Blood. 2006:108 (the entire contents of which are incorporated herein by reference)), or a CD40 agonist peptide or small molecule. Exemplary suitable CD40 agonists are provided herein and additional suitable CD40 agonists will be apparent to those of ordinary skill in the art based on the present disclosure.

The disclosure is not limited in this respect. In some embodiments, the disclosure provides methods for treating a cancer in a subject that comprises administering tazemetostat and a CD40 agonist to the subject. In some embodiments, the cancer is not sensitive to treatment with a monotherapy, e.g., to treatment with tazemetostat alone or to treatment with a CD40 agonist alone.

In some embodiments, the cancer is adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenström macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, or Wilm's Tumor.

In some embodiments, the EZH2 inhibitor is an EZH2 inhibitor as provided herein, e.g., tazemetostat. In certain embodiments, the EZH2 inhibitor is a is CPI-1205 or GSK343.

Additional suitable EZH2 inhibitors, e.g., GSK126, GSK343, CPI-1205, and others, will be apparent to those skilled in the art based on the present disclosure. In some embodiments of the strategies, treatment modalities, methods, combinations, and compositions provided herein, the EZH2 inhibitor is an EZH2 inhibitor described in U.S. Pat. No. 8,536,179 (describing GSK-126 among other compounds and corresponding to WO 2011/140324), the entire contents of each of which are incorporated herein by reference.

In some embodiments of the strategies, treatment modalities, methods, combinations, and compositions provided herein, the EZH2 inhibitor is an EZH2 inhibitor described in PCT/US2014/015706, published as WO 2014/124418, in PCT/US2013/025639, published as WO 2013/120,104, and in U.S. Ser. No. 14/839,273, published as US 2015/0368229, the entire contents of each of which are incorporated herein by reference. In some embodiments, the cancer is germinal center-derived lymphoma, e.g., a germinal center B-cell lymphoma. In some embodiments, the germinal center B-cell lymphoma is an EZH2 wild type germinal center B-cell lymphoma, e.g., the germinal center B-cell lymphoma cells having non-mutated, wild-type EZH2 protein.

In another embodiment, the germinal center B-cell lymphoma is an EZH2 mutant germinal center B-cell lymphoma, e.g., the germinal center B-cell lymphoma cells having mutant EZH2 protein.

In some embodiments, the germinal center B-cell lymphoma is diffuse large B-cell lymphoma (DLBCL), follicular lymphoma, Burkitt's lymphoma or Non-Hodgkin's Lymphoma of germinal center B cell type.

In some embodiments, the EZH2 inhibitor is administered orally.

In some embodiments, the subject is a human being.

In some embodiments, the EZH2 inhibitor is of formula (I) below, or a pharmaceutically acceptable salt thereof:

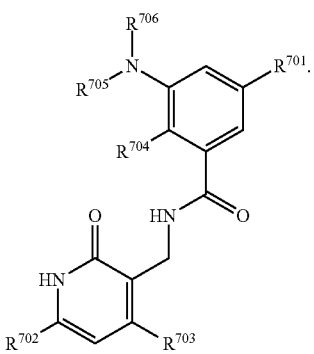

(I)

In Formula (I), $R^{701}$ is H, F, $OR^{707}$, $NHR^{707}$, —(C≡C)—$(CH_2)_{n7}$—$R^{708}$, phenyl, 5- or 6-membered heteroaryl, $C_{3-8}$ cycloalkyl, or 4-7 membered heterocycloalkyl containing 1-3 heteroatoms, wherein the phenyl, 5- or 6-membered heteroaryl, $C_{3-8}$ cycloalkyl or 4-7 membered heterocycloalkyl each independently is optionally substituted with one or more groups selected from halo, $C_{1-3}$ alkyl, OH, O—$C_{1-6}$ alkyl, NH—$C_{1-6}$ alkyl, and, $C_{1-3}$ alkyl substituted with $C_{3-8}$ cycloalkyl or 4-7 membered heterocycloalkyl containing 1-3 heteroatoms, wherein each of the O—$C_{1-6}$ alkyl and NH—$C_{1-6}$ alkyl is optionally substituted with hydroxyl, O—$C_{1-3}$ alkyl or NH—$C_{1-3}$ alkyl, each of the O—$C_{1-3}$ alkyl and NH—$C_{1-3}$ alkyl being optionally further substituted with O—$C_{1-3}$ alkyl or NH—$C_{1-3}$ alkyl; each of $R^{702}$ and $R^{703}$, independently is H, halo, $C_{1-4}$ alkyl, $C_{1-6}$ alkoxyl or $C_6$-$C_{10}$ aryloxy, each optionally substituted with one or more halo; each of $R^{704}$ and $R^{705}$, independently is $C_{1-4}$ alkyl; $R^{706}$ is cyclohexyl substituted by $N(C_{1-4}$ alkyl$)_2$ wherein one or both of the $C_{1-4}$ alkyl is optionally substituted with $C_{1-6}$ alkoxy; or $R^{706}$ is tetrahydropyranyl; $R^{707}$ is $C_{1-4}$ alkyl optionally substituted with one or more groups selected from hydroxyl, $C_{1-4}$ alkoxy, amino, mono- or di-$C_{1-4}$ alkylamino, $C_{3-8}$ cycloalkyl, and 4-7 membered heterocycloalkyl containing 1-3 heteroatoms, wherein the $C_{3-8}$ cycloalkyl or 4-7 membered heterocycloalkyl each independently is further optionally substituted with $C_{1-3}$ alkyl; $R^{708}$ is $C_{1-4}$ alkyl optionally substituted with one or more groups selected from OH, halo, and $C_{1-4}$ alkoxy, 4-7 membered heterocycloalkyl containing 1-3 heteroatoms, or O—$C_{1-6}$ alkyl, wherein the 4-7 membered heterocycloalkyl can be optionally further substituted with OH or $C_{1-6}$ alkyl; and $n_7$ is 0, 1 or 2.

In some embodiments, the EZH2 inhibitor is EPZ-6438, having the following formula:

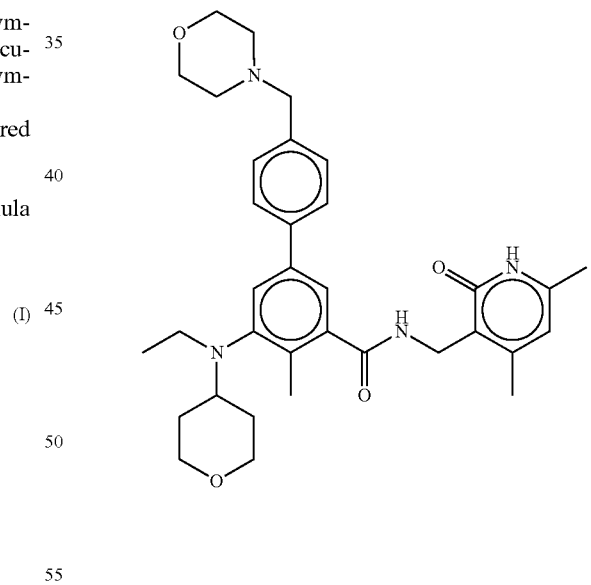

or a pharmaceutically acceptable salt thereof.

In some embodiments, the EZH2 inhibitor is administered to the subject at a dose of approximately 100 mg to approximately 3,200 mg daily.

In some embodiments, the EZH2 inhibitor is administered to the subject at a dose of approximately 100 mg BID to approximately 1,600 mg BID.

In some embodiments, the EZH2 inhibitor is administered to the subject at a dose of approximately 100 mg BID, 200 mg BID, 400 mg BID, 800 mg BID, or 1,600 mg BID.

In some embodiments, the EZH2 inhibitor is either compound (A), (B), (C) or (D):

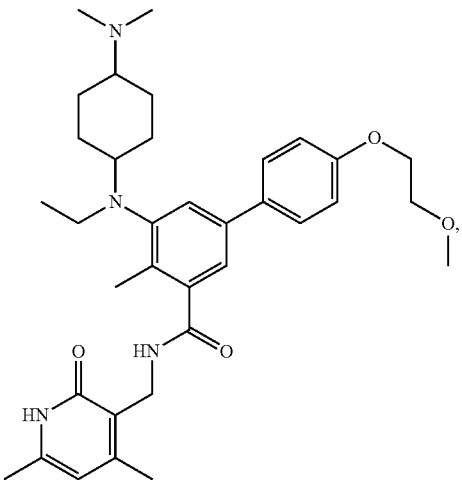
(A)

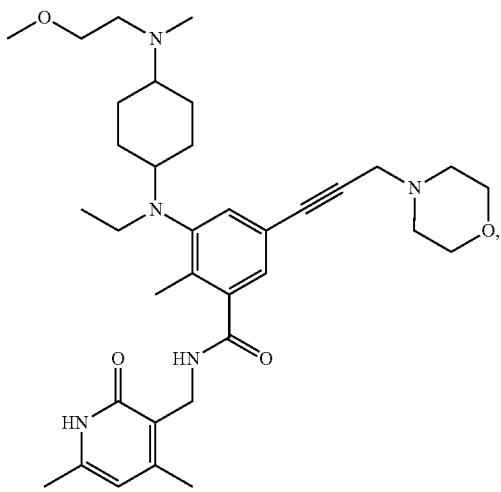
(B)

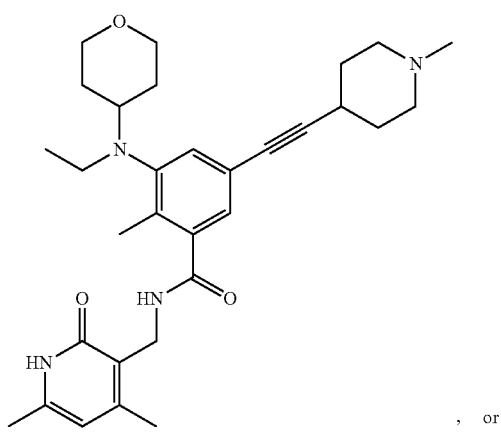
(C)

, or

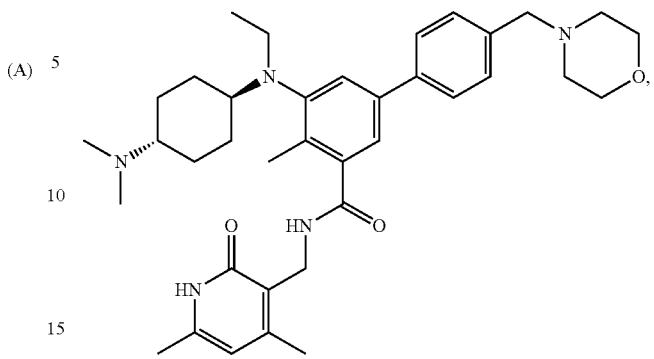
(D)

or pharmaceutically acceptable salts or solvates thereof.

In some embodiments, the method further includes administering a therapeutically effective amount of a second therapeutic agent, such as one or more components of R—CHOP, a BCL inhibitor, or a BCR inhibitor.

In some embodiments, the EZH2 inhibitor is administered simultaneously or sequentially with the second therapeutic agent.

In some embodiments, the EZH2 inhibitor is administered prior to the administration of the second therapeutic agent.

In some embodiments, the second therapeutic agent is administered prior to the administration of the EZH2 inhibitor.

In another aspect, the present disclosure features a method for the treatment or prevention of Primary Mediastinal Large B-Cell Lymphoma (PMBCL) in a subject in need thereof. The method includes administration of a therapeutically effective amount of an EZH2 inhibitor to said subject.

The method can include one or more of the following features.

In some embodiments, the PMBCL is a mutant EZH2
In some embodiments, the PMBCL is wild-type EZH2.
In some embodiments, the EZH2 inhibitor is administered orally.
In some embodiments, the subject is a human being.
In some embodiments, the EZH2 inhibitor is of formula (I) below, or a pharmaceutically acceptable salt thereof:

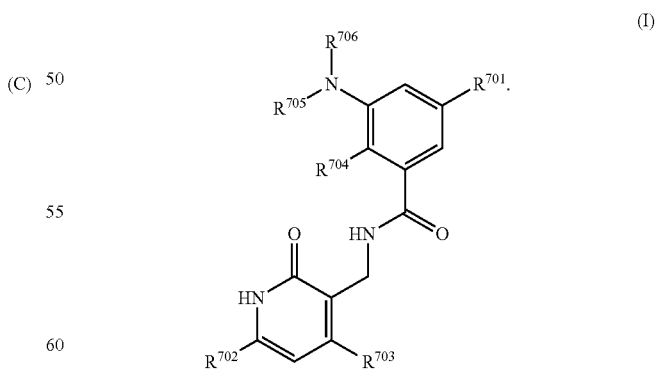
(I)

In Formula (I), $R^{701}$ is H, F, $OR^{707}$, $NHR^{707}$, —(C≡C)—$(CH_2)_{n7}$—$R^{708}$, phenyl, 5- or 6-membered heteroaryl, $C_{3-8}$ cycloalkyl, or 4-7 membered heterocycloalkyl containing 1-3 heteroatoms, wherein the phenyl, 5- or 6-membered heteroaryl, $C_{3-8}$ cycloalkyl or 4-7 membered heterocycloalkyl each independently is optionally substituted with one or more groups selected from halo, $C_{1-3}$ alkyl, OH, O—$C_{1-6}$ alkyl, NH—$C_{1-6}$ alkyl, and, $C_{1-3}$ alkyl substituted with $C_{3-8}$ cycloalkyl or 4-7 membered heterocycloalkyl containing 1-3 heteroatoms, wherein each of the O—$C_{1-6}$ alkyl and NH—$C_{1-6}$ alkyl is optionally substituted with hydroxyl, O—$C_{1-3}$ alkyl or NH—$C_{1-3}$ alkyl, each of the O—$C_{1-3}$ alkyl and NH—$C_{1-3}$ alkyl being optionally further substituted with O—$C_{1-3}$ alkyl or NH—$C_{1-3}$ alkyl; each of $R^{702}$ and $R^{703}$, independently is H, halo, $C_{1-4}$ alkyl, $C_{1-6}$ alkoxyl or $C_6$-$C_{10}$ aryloxy, each optionally substituted with one or more halo; each of $R^{704}$ and $R^{705}$, independently is $C_{1-4}$ alkyl; $R^{706}$ is cyclohexyl substituted by N($C_{1-4}$ alkyl)$_2$ wherein one or both of the $C_{1-4}$ alkyl is optionally substituted with $C_{1-6}$ alkoxy; or $R^{706}$ is tetrahydropyranyl; $R^{707}$ is $C_{1-4}$ alkyl optionally substituted with one or more groups selected from hydroxyl, $C_{1-4}$ alkoxy, amino, mono- or di-$C_{1-4}$ alkylamino, $C_{3-8}$ cycloalkyl, and 4-7 membered heterocycloalkyl containing 1-3 heteroatoms, wherein the $C_{3-8}$ cycloalkyl or 4-7 membered heterocycloalkyl each independently is further optionally substituted with $C_{1-3}$ alkyl; $R^{708}$ is $C_{1-4}$ alkyl optionally substituted with one or more groups selected from OH, halo, and $C_{1-4}$ alkoxy, 4-7 membered heterocycloalkyl containing 1-3 heteroatoms, or O—$C_{1-6}$ alkyl, wherein the 4-7 membered heterocycloalkyl can be optionally further substituted with OH or $C_{1-6}$ alkyl; and $n_7$ is 0, 1 or 2.

In some embodiments, the EZH2 inhibitor is EPZ-6438, having the following formula:

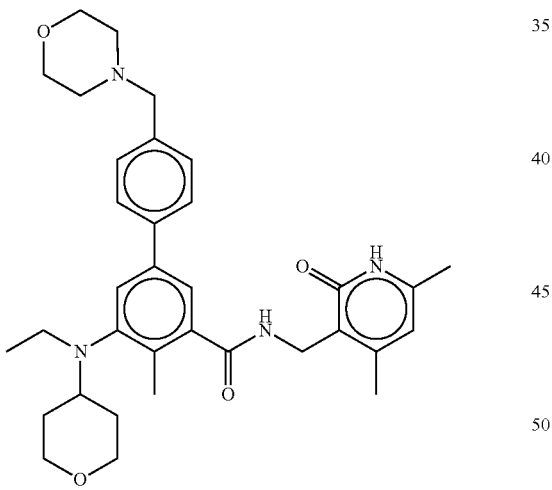

or a pharmaceutically acceptable salt thereof.

In some embodiments, the EZH2 inhibitor is administered to the subject at a dose of approximately 100 mg to approximately 3,200 mg daily.

In some embodiments, the EZH2 inhibitor is administered to the subject at a dose of approximately 100 mg BID to approximately 1,600 mg BID.

In some embodiments, the EZH2 inhibitor is administered to the subject at a dose of approximately 100 mg BID, 200 mg BID, 400 mg BID, 800 mg BID, or 1,600 mg BID.

In some embodiments, the EZH2 inhibitor is either compound (A), (B), or (C):

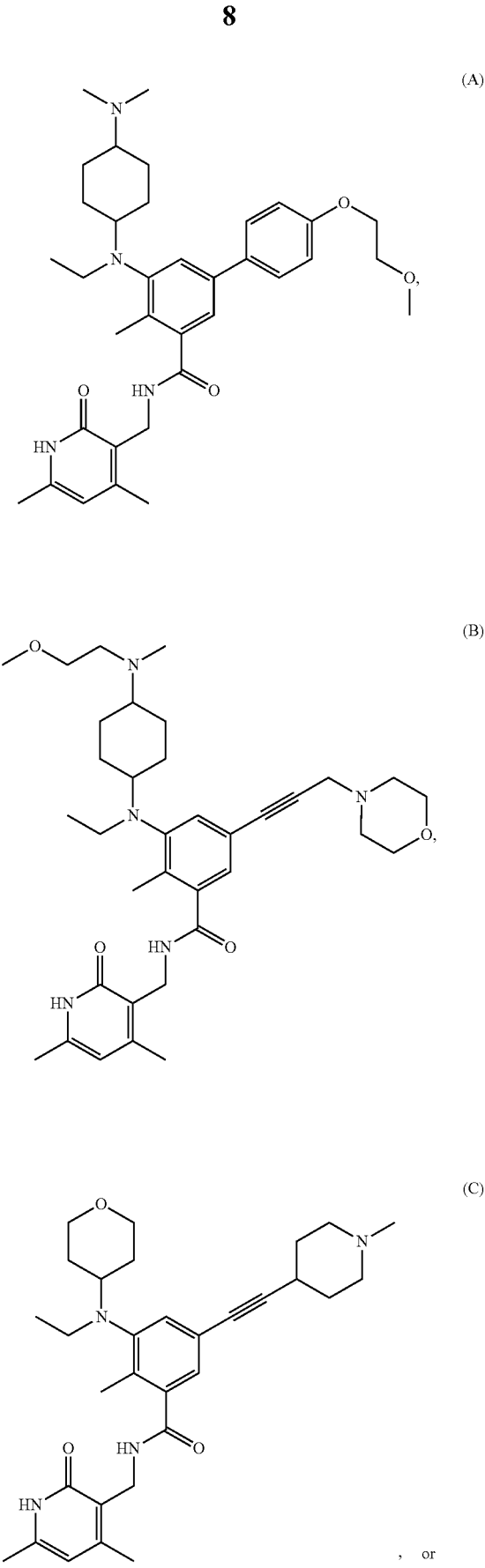

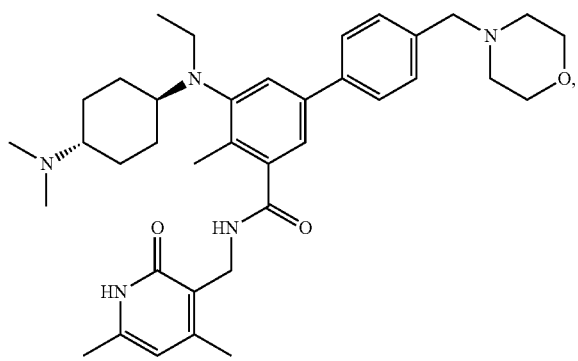

(D)

or pharmaceutically acceptable salts or solvates thereof.

In some embodiments, the method further includes administering a therapeutically effective amount of a second therapeutic agent, such as one or more components of R—CHOP, a BCL inhibitor, or a BCR inhibitor.

In some embodiments, the EZH2 inhibitor is administered simultaneously or sequentially with the second therapeutic agent.

In some embodiments, the EZH2 inhibitor is administered prior to the administration of the second therapeutic agent.

In some embodiments, the second therapeutic agent is administered prior to the administration of the EZH2 inhibitor.

In another aspect, the disclosure also relates to a method of selecting a patient for the methods of treating cancer described herein, by selecting the patient based on the expression profiles of one or more genes selected from the group consisting of EZH2, BCL6 and BCL2.

In any of the above aspects or embodiments, the disclosure also relates to detecting levels of histone methylation, e.g., H3K27 trimethylation, in a skin biopsy. Histone methylation is detected prior to initiation of treatment, while the subject is receiving treatment, and/or after treatment has concluded. Detecting histone methylation via skin biopsy Any of the above aspects and embodiments can be combined with any other aspect or embodiment.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the disclosure will be apparent from the following detailed description and claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and further features will be more clearly appreciated from the following detailed description when taken in conjunction with the accompanying drawings.

FIG. 8. Chart providing synergistic relationships (same as Table 1 but in color).

DETAILED DESCRIPTION

Figure 1:
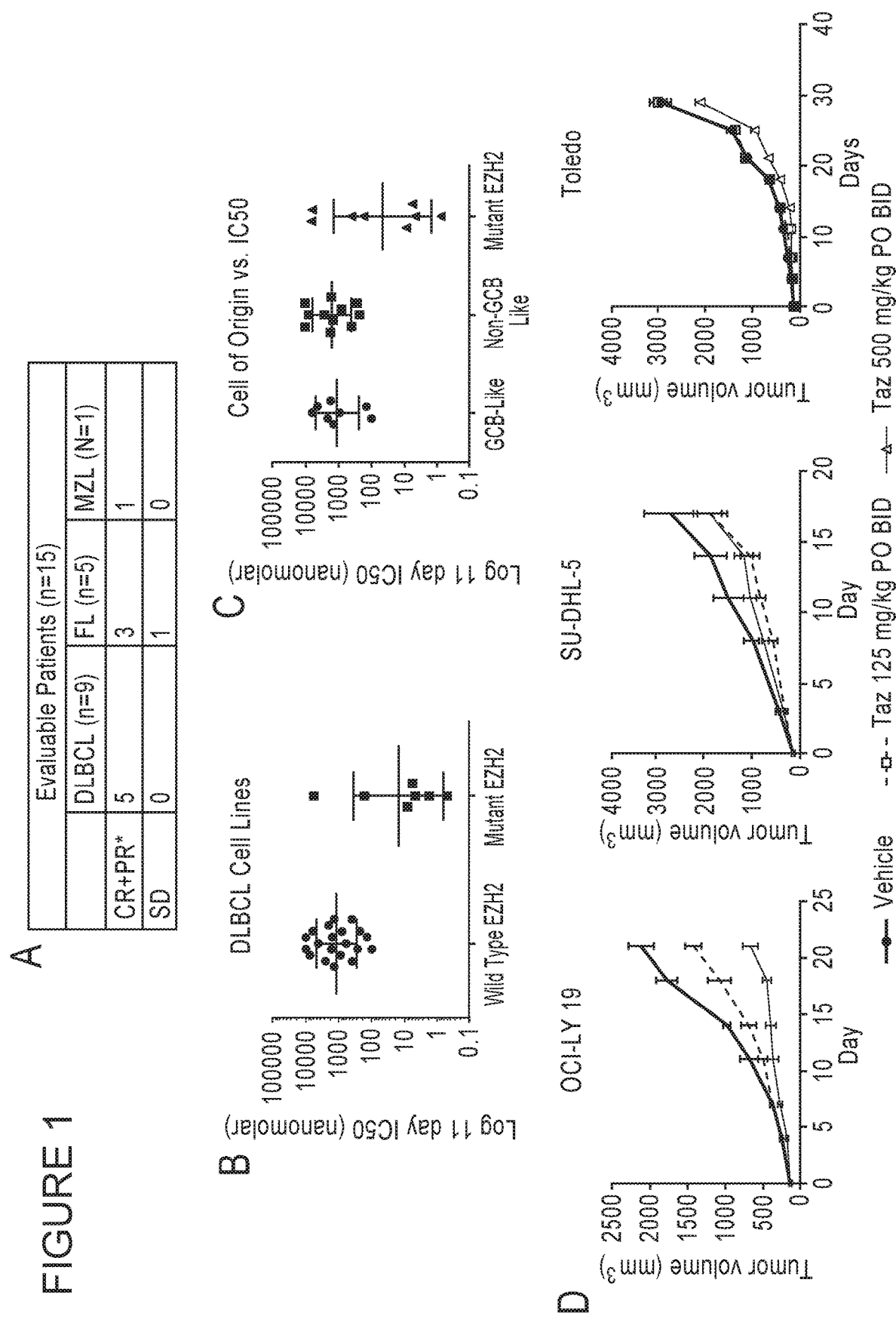
FIG. 1. Effects of tazemetostat (TAZ) in vivo suggest that an additional anti-tumor mechanism occurs beyond what is observed in vitro.

EZH2 is a histone methyltransferase that is the catalytic subunit of the PRC2 complex which catalyzes the mono-through tri-methylation of lysine 27 on histone H3 (H3-K27). Histone H3-K27 trimethylation is a mechanism for suppressing transcription of specific genes that are proximal to the site of histone modification. This trimethylation is known to be a cancer marker with altered expression in cancer, such as prostate cancer (see, e.g., U.S. Patent Application Publication No. 2003/0175736; incorporated herein by reference in its entirety). Other studies provided evidence for a functional link between dysregulated EZH2 expression, transcriptional repression, and neoplastic transformation. Varambally et al. (2002) *Nature* 419(6907):624-9 Kleer et al. (2003) *Proc Natl Acad Sci USA* 100(20):11606-11.

EZH2 methylation activity plays an important role in the regulation and activation of germinal center B-cells. EZH2 protein levels increase following the activation of B-cells. Following activation, B-cells take residence in the germinal center of lymphoid organs, wherein somatic hypermutation occurs, a process associated with the repression of anti-apoptotic genes and check point regulators. EZH2 methylating events target genes that are involved in B-cell proliferation, differentiation and maturation, including CDKN1A (role in cellular proliferation), PRDM1 (role in B-cell differentiation) and IRF4 (role in B-cell differentiation).

Following the maturation and exit of B-cells from the germinal center, there is a reduction of the levels of EZH2 within the B-cells. However, EZH2 presence and activity after B-cell maturation is associated with several kinds of lymphomas including germinal center B-cell lymphoma, among others. Aberrant activation of EZH2 is found in three common subtypes of germinal cell lymphomas: follicular lymphoma (FL), germinal center B-cell like diffuse large B-cell lymphoma (GCB DLBCL), and Burkitt's lymphoma.

Aberrant activation of EZH2 is also found in Primary Mediastinal Large B-Cell Lymphoma (PMBCL).

Genetic alterations within the EZH2 gene are associated with altered histone methylation patterns. EZH2 mutations leading to the conversion of amino acid Y641 (equivalent to Y646, catalytic domain), to either F, N, H, S or C results in hypertrimethylation of H3K27 and drives lymphomagenesis. Additional genetic alterations that affect the methylation of H3K27 include EZH2 SET-domain mutations, overexpression of EZH2, overexpression of other PRC2 subunits, loss of function mutations of histone acetyl transferases (HATs), and loss of function of MLL2. Cells that are heterozygous for EZH2 Y646 mutations result in hypertrimethylation of H3K27 relative to cells that are homozygous wild-type (WT) for the EZH2 protein, or to cells that are homozygous for the Y646 mutation.

This disclosure is based on, at least in part, discoveries that (i) EZH2 mutant germinal B-cell lines are consistently sensitive to EZH2 inhibitors; (ii) EZH2 wild-type (WT) germinal B-cell lymphoma cell lines are sensitive to EZH2 inhibitors, in a dose-dependent manner; and (iii) activated B-cell lymphoma (ABC-lymphoma) cell lines are not sensitive to EZH2 inhibitors.

An aspect of the present disclosure relates to a method for treating or alleviating a symptom of a germinal center-derived lymphoma in a subject in need thereof by administering to the subject a therapeutically effective amount of an EZH2 inhibitor. The subject suitable for the method of treatment described herein can either express a mutant EZH2 or a wild-type EZH2 or has a mutation in the EZH2 gene or has a wild-type EZH2 gene.

As described herein, inhibition of EZH2 activity significantly abrogates the division of the malignant cells.

In some embodiments, the germinal center B-cell lymphoma is an EZH2 wild type germinal center B-cell lymphoma, e.g., the germinal center B-cell lymphoma cells having non-mutated, wild-type EZH2 protein.

In another embodiment, the germinal center B-cell lymphoma is an EZH2 mutant germinal center B-cell lymphoma, e.g., the germinal center B-cell lymphoma cells having mutant EZH2 protein.

In some embodiments, the germinal center B-cell lymphoma is diffuse large B-cell lymphoma, follicular lymphoma, Burkitt's lymphoma or Non-Hodgkin's Lymphoma of germinal center B cell type.

In some embodiments, the EZH2 inhibitor is administered orally.

In some embodiments, the subject is a human being.

In some embodiments, the method further includes administering a therapeutically effective amount of a second therapeutic agent, such as one or more components of R—CHOP, a BCL inhibitor, or a BCR inhibitor.

In some embodiments, the EZH2 inhibitor is administered simultaneously or sequentially with the second therapeutic agent.

In some embodiments, the EZH2 inhibitor is administered prior to the administration of the second therapeutic agent.

In some embodiments, the second therapeutic agent is administered prior to the administration of the EZH2 inhibitor.

Another aspect of the present disclosure relates to a method for treating or alleviating a symptom of Primary Mediastinal Large B-Cell Lymphoma (PMBCL) in a subject in need thereof by administering to the subject a therapeutically effective amount of an EZH2 inhibitor. The subject suitable for the method of treatment described herein can have a mutant EZH2 or a wild-type EZH2. As described herein, inhibition of EZH2 activity significantly abrogates the division of the malignant cells.

In some embodiments, the PMBCL is a mutant EZH2

In some embodiments, the PMBCL is wild-type EZH2.

In some embodiments, the EZH2 inhibitor is administered orally.

In some embodiments, the subject is a human being.

In some embodiments, the method further includes administering a therapeutically effective amount of a second therapeutic agent, such as one or more components of R—CHOP, a BCL inhibitor, or a BCR inhibitor.

In some embodiments, the EZH2 inhibitor is administered simultaneously or sequentially with the second therapeutic agent.

In some embodiments, the EZH2 inhibitor is administered prior to the administration of the second therapeutic agent.

In some embodiments, the second therapeutic agent is administered prior to the administration of the EZH2 inhibitor.

In any of the above aspects or embodiments, the disclosure also relates to methods for detecting levels of histone methylation, e.g., H3K27 trimethylation, in a skin biopsy. Histone methylation is detected prior to initiation of treatment, while the subject is receiving treatment, and/or after treatment has concluded.

The mutant EZH2 described herein refers to a mutant EZH2 polypeptide or a nucleic acid sequence encoding a mutant EZH2 polypeptide. In certain embodiments the mutant EZH2 comprises one or more mutations in its substrate pocket domain. For example, the mutation may be a substitution, a point mutation, a nonsense mutation, a missense mutation, a deletion, or an insertion. Methods for detecting EZH2 mutations have been described in PCT/US11/051258, PCT/US13/030565, US20150099747, each of which is incorporated herein by reference in its entirety.

For purposes of this application, a Y641 mutant of human EZH2, and, equivalently, a Y641 mutant of EZH2, is to be understood to refer to a human EZH2 in which the amino acid residue corresponding to Y641 of wild-type human EZH2 is substituted by an amino acid residue other than tyrosine.

A compound (i.e., an EZH2 inhibitor) that can be used in any methods described herein may have the following Formula (I):

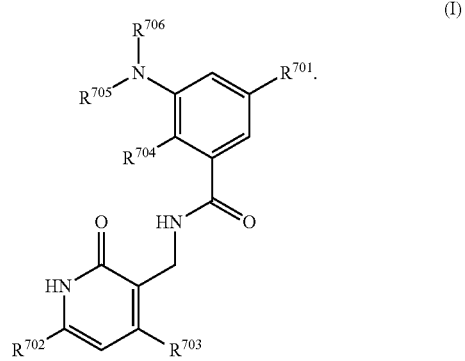

or a pharmaceutically acceptable salt thereof; wherein
$R^{701}$ is H, F, $OR^{707}$, $NHR^{707}$, —(C≡C)—$(CH_2)_{n7}$—$R^{708}$, phenyl, 5- or 6-membered heteroaryl, $C_{3-8}$ cycloalkyl, or 4-7 membered heterocycloalkyl containing 1-3 heteroatoms, wherein the phenyl, 5- or 6-membered heteroaryl, $C_{3-8}$ cycloalkyl or 4-7 membered heterocycloalkyl each independently is optionally substituted with one or more groups selected from halo, $C_{1-3}$ alkyl, OH, O—$C_{1-6}$ alkyl, NH—$C_{1-6}$ alkyl, and, $C_{1-3}$ alkyl substituted with $C_{3-8}$ cycloalkyl or 4-7 membered heterocycloalkyl containing 1-3 heteroatoms, wherein each of the O—$C_{1-6}$ alkyl and NH—$C_{1-6}$ alkyl is optionally substituted with hydroxyl, O—C$_{1-3}$ alkyl or NH—C$_{1-3}$ alkyl, each of the O—C$_{1-3}$ alkyl and NH—C$_{1-3}$ alkyl being optionally further substituted with O—C$_{1-3}$ alkyl or NH—C$_{1-3}$ alkyl;

each of R$^{702}$ and R$^{703}$, independently is H, halo, C$_{1-4}$ alkyl, C$_{1-6}$ alkoxyl or C$_6$-C$_{10}$ aryloxy, each optionally substituted with one or more halo;

each of R$^{704}$ and R$^{705}$, independently is C$_{1-4}$ alkyl;

R$^{706}$ is cyclohexyl substituted by N(C$_{1-4}$ alkyl)$_2$ wherein one or both of the C$_{1-4}$ alkyl is optionally substituted with C$_{1-6}$alkoxy; or R$^{706}$ is tetrahydropyranyl;

R$^{707}$ is C$_{1-4}$ alkyl optionally substituted with one or more groups selected from hydroxyl, C$_{1-4}$ alkoxy, amino, mono- or di-C$_{1-4}$ alkylamino, C$_{3-8}$ cycloalkyl, and 4-7 membered heterocycloalkyl containing 1-3 heteroatoms, wherein the C$_{3-8}$ cycloalkyl or 4-7 membered heterocycloalkyl each independently is further optionally substituted with C$_{1-3}$ alkyl;

R$^{708}$ is C$_{1-4}$ alkyl optionally substituted with one or more groups selected from OH, halo, and C$_{1-4}$ alkoxy, 4-7 membered heterocycloalkyl containing 1-3 heteroatoms, or O—C$_{1-6}$ alkyl, wherein the 4-7 membered heterocycloalkyl can be optionally further substituted with OH or C$_{1-6}$ alkyl; and n$_7$ is 0, 1 or 2.

For example, R$^{706}$ is cyclohexyl substituted by N(C$_{1-4}$ alkyl)$_2$ wherein one of the C$_{1-4}$ alkyl is unsubstituted and the other is substituted with methoxy.

For example, R$^{706}$ is

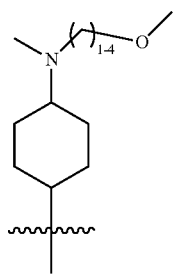

For example, the compound is of Formula II:

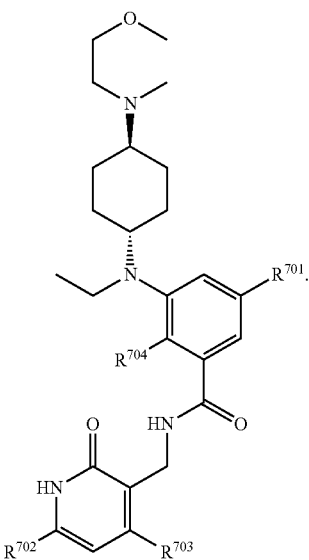

(II)

For example, R$^{702}$ is methyl or isopropyl and R$^{703}$ is methyl or methoxyl.

For example, R$^{704}$ is methyl.

For example, R$^{701}$ is OR$^{707}$ and R$^{707}$ is C$_{1-3}$ alkyl optionally substituted with OCH$_3$ or morpholine.

For example, R$^{701}$ is H or F.

For example, R$^{701}$ is tetrahydropyranyl, phenyl, pyridyl, pyrimidyl, pyrazinyl, imidazolyl, or pyrazolyl, each of which is optionally substituted with methyl, methoxy, ethyl substituted with morpholine, or —OCH$_2$CH$_2$OCH$_3$.

For example, R$^{708}$ is morpholine, piperidine, piperazine, pyrrolidine, diazepane, or azetidine, each of which is optionally substituted with OH or C$_{1-6}$ alkyl.

For example, R$^{708}$ is morpholine

For example, R$^{708}$ is piperazine substituted with C$_{1-6}$ alkyl.

For example, R$^{708}$ is methyl, t-butyl or C(CH$_3$)$_2$OH.

A compound (i.e., an EZH2 inhibitor) that can be used in any methods described herein may have the following Formula III:

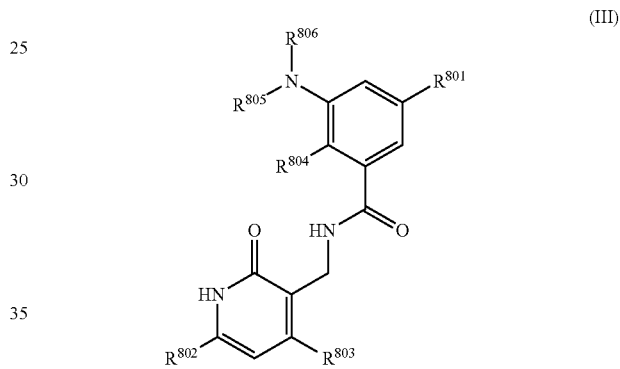

(III)

or a pharmaceutically acceptable salt thereof.

In this formula:

R$^{801}$ is C$_{1-6}$ alkyl, C$_{2-6}$ alkenyl, C$_{2-6}$ alkynyl, C$_{3-8}$ cycloalkyl, 4-7 membered heterocycloalkyl containing 1-3 heteroatoms, phenyl or 5- or 6-membered heteroaryl, each of which is substituted with O—C$_{1-6}$ alkyl-R$_x$ or NH—C$_{1-6}$ alkyl-R$_x$, wherein R$_x$ is hydroxyl, O—C$_{1-3}$ alkyl or NH—C$_{1-3}$ alkyl, and R$_x$ is optionally further substituted with O—C$_{1-3}$ alkyl or NH—C$_{1-3}$ alkyl except when R$_x$ is hydroxyl; or R$^{801}$ is phenyl substituted with —Q$_2$—T$_2$, wherein Q$_2$ is a bond or C$_1$-C$_3$ alkyl linker optionally substituted with halo, cyano, hydroxyl or C$_1$-C$_6$ alkoxy, and T$_2$ is optionally substituted 4- to 12-membered heterocycloalkyl; and R$^{801}$ is optionally further substituted;

each of R$^{802}$ and R$^{803}$, independently is H, halo, C$_{1-4}$ alkyl, C$_{1-6}$ alkoxyl or C$_6$-C$_{10}$ aryloxy, each optionally substituted with one or more halo;

each of R$^{804}$ and R$^{805}$, independently is C$_{1-4}$ alkyl; and

R$^{806}$ is —Q$_x$—T$_x$, wherein Q$_x$ is a bond or C$_{1-4}$ alkyl linker, T$_x$ is H, optionally substituted C$_{1-4}$ alkyl, optionally substituted C$_3$-C$_8$ cycloalkyl or optionally substituted 4- to 14-membered heterocycloalkyl.

For example, each of Q$_x$ and Q$_2$ independently is a bond or methyl linker, and each of T$_x$ and T$_2$ independently is tetrahydropyranyl, piperidinyl substituted by 1, 2, or 3 C$_{1-4}$ alkyl groups, or cyclohexyl substituted by N(C$_{1-4}$ alkyl)$_2$ wherein one or both of the C$_{1-4}$ alkyl is optionally substituted with C$_{1-6}$ alkoxy;

For example, $R^{806}$ is cyclohexyl substituted by $N(C_{1-4}$ alkyl$)_2$ or $R^{806}$ is tetrahydropyranyl.

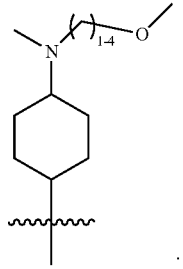

For example, $R^{806}$ is

For example, $R^{801}$ is phenyl or 5- or 6-membered heteroaryl substituted with $O-C_{1-6}$ alkyl-$R_x$, or $R^{801}$ is phenyl substituted with $CH_2$-tetrahydropyranyl.

For example, a compound of the present disclosure is of Formula IVa or IVb:

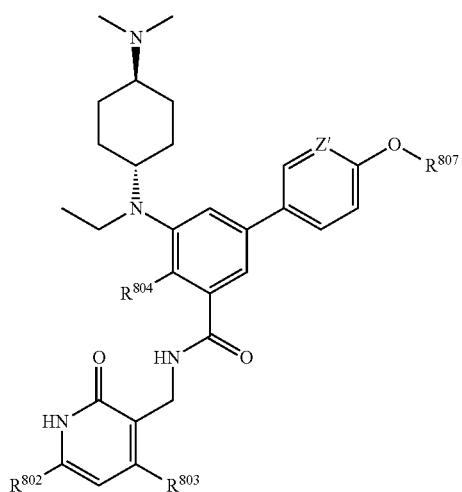
(IVa)

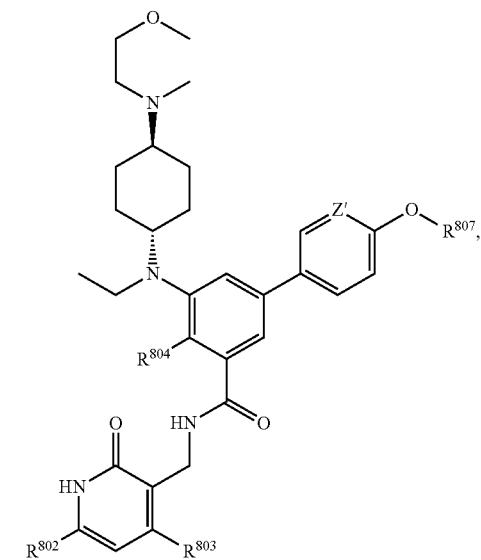
(IVb)

wherein
Z' is CH or N, and $R^{807}$ is $C_{2-3}$ alkyl-$R_x$.

For example, $R^{807}$ is $-CH_2CH_2OH$, $-CH_2CH_2OCH_3$, or $-CH_2CH_2OCH_2CH_2OCH_3$.

For example, $R^{802}$ is methyl or isopropyl and $R^{803}$ is methyl or methoxy.

For example, $R^{804}$ is methyl.

A compound of the present disclosure may have the following Formula (V):

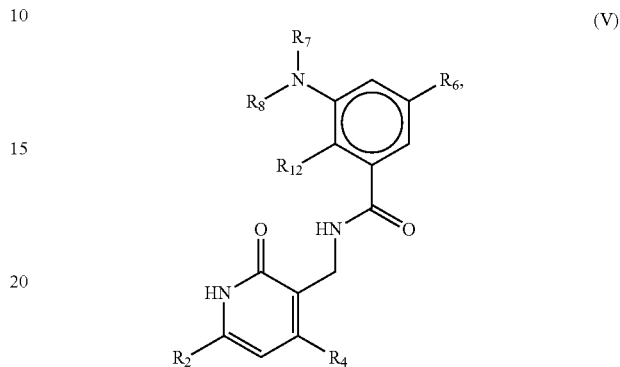
(V)

or a pharmaceutically acceptable salt or ester thereof.

In this formula:

$R_2$, $R_4$ and $R_{12}$ are each, independently $C_{1-6}$ alkyl;

$R_6$ is $C_6$-$C_{10}$ aryl or 5- or 6-membered heteroaryl, each of which is optionally substituted with one or more $-Q_2-T_2$, wherein $Q_2$ is a bond or $C_1$-$C_3$ alkyl linker optionally substituted with halo, cyano, hydroxyl or $C_1$-$C_6$ alkoxy, and $T_2$ is H, halo, cyano, $-OR_a$, $-NR_aR_b$, $-(NR_aR_bR_c)^+A^-$, $-C(O)R_a$, $-C(O)OR_a$, $-C(O)NR_aR_b$, $-NR_bC(O)R_a$, $-NR_bC(O)OR_a$, $-S(O)_2R_a$, $-S(O)_2NR_aR_b$, or $R_{S2}$, in which each of $R_a$, $R_b$, and $R_c$, independently is H or $R_{S3}$, A$^-$ is a pharmaceutically acceptable anion, each of $R_{S2}$ and $R_{S3}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_a$ and $R_b$, together with the N atom to which they are attached, form a 4 to 12-membered heterocycloalkyl ring having 0 or 1 additional heteroatom, and each of $R_{S2}$, $R_{S3}$, and the 4 to 12-membered heterocycloalkyl ring formed by $R_a$ and $R_b$, is optionally substituted with one or more $-Q_3-T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_d$, $COOR_d$, $-S(O)_2R_d$, $-NR_dR_e$, and $-C(O)NR_dR_e$, each of $R_d$ and $R_e$ independently being H or $C_1$-$C_6$ alkyl, or $-Q_3-T_3$ is oxo; or any two neighboring $-Q_2-T_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O$-C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_7$ is $-Q_4-T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_fR_g$, $-OR_f$, $-C(O)R_f$, $-C(O)OR_f$, $-C(O)NR_fR_g$, $-C(O)NR_fOR_g$, $-NR_fC(O)R_g$, $-S(O)_2R_f$ or $R_{S4}$, in which each of $R_f$ and $R_g$, independently is H or $R_{S5}$, each of $R_{S4}$ and $R_{S5}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and each of $R_{S4}$ and $R_{S5}$ is optionally substituted with one or more —$Q_5$—$T_5$, wherein $Q_5$ is a bond, C(O), C(O)NR$_k$, NR$_k$C(O), S(O)$_2$, or $C_1$-$C_3$ alkyl linker, R$_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or S(O)$_q$R$_q$ in which q is 0, 1, or 2 and R$_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or —$Q_5$—$T_5$ is oxo; and $R_8$ is H, halo, hydroxyl, COOH, cyano, $R_{S6}$, OR$_{S6}$, or COOR$_{S6}$, in which R$_{S6}$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and R$_{S6}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 11-membered heterocycloalkyl ring having 0 to 2 additional heteroatoms, and the 4 to 11-membered heterocycloalkyl ring formed by $R_7$ and $R_8$ is optionally substituted with one or more —$Q_6$—$T_6$, wherein $Q_6$ is a bond, C(O), C(O)NR$_m$, NR$_m$C(O), S(O)$_2$, or $C_1$-$C_3$ alkyl linker, R$_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or S(O)$_p$R$_p$ in which p is 0, 1, or 2 and R$_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6$ is H, halo, hydroxyl, or cyano; or —$Q_6$—$T_6$ is oxo.

For example, $R_6$ is $C_6$-$C_{10}$ aryl or 5- or 6-membered heteroaryl, each of which is optionally, independently substituted with one or more —$Q_2$—$T_2$, wherein $Q_2$ is a bond or $C_1$-$C_3$ alkyl linker, and $T_2$ is H, halo, cyano, —OR$_a$, —NR$_a$R$_b$, —(NR$_a$R$_b$R$_c$)$^+$A$^-$, —C(O)NR$_a$R$_b$, —NR$_a$C(O)R$_a$, —S(O)$_2$R$_a$, or R$_{S2}$, in which each of R$_a$ and R$_b$, independently is H or R$_{S3}$, each of R$_{S2}$ and R$_{S3}$, independently, is $C_1$-$C_6$ alkyl, or R$_a$ and R$_b$, together with the N atom to which they are attached, form a 4 to 7-membered heterocycloalkyl ring having 0 or 1 additional heteroatom, and each of R$_{S2}$, R$_{S3}$, and the 4 to 7-membered heterocycloalkyl ring formed by R$_a$ and R$_b$, is optionally, independently substituted with one or more —$Q_3$—$T_3$, wherein $Q_3$ is a bond or $C_1$-$C_3$ alkyl linker and $T_3$ is selected from the group consisting of halo, $C_1$-$C_6$ alkyl, 4 to 7-membered heterocycloalkyl, OR$_d$, —S(O)$_2$R$_d$, and —NR$_d$R$_e$, each of R$_d$ and R$_e$ independently being H or $C_1$-$C_6$ alkyl, or —$Q_3$—$T_3$ is oxo; or any two neighboring —$Q_2$—$T_2$, together with the atoms to which they are attached form a 5- or 6-membered ring optionally containing 1-4 heteroatoms selected from N, O and S.

For example, the compound of the present disclosure is of Formula (VI):

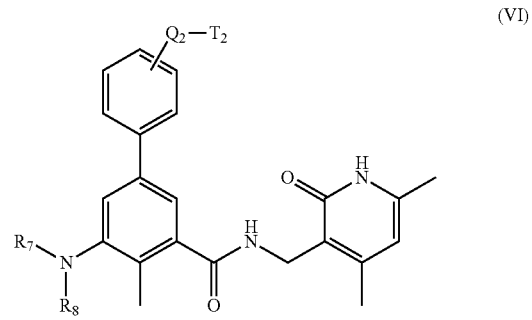

(VI)

or a pharmaceutically acceptable salt thereof, wherein $Q_2$ is a bond or methyl linker, $T_2$ is H, halo, —OR$_a$, —NR$_a$R$_b$, —(NR$_a$R$_b$R$_c$)$^+$A$^-$, or —S(O)$_2$NR$_a$R$_b$, R$_7$ is piperidinyl, tetrahydropyran, cyclopentyl, or cyclohexyl, each optionally substituted with one —$Q_5$—$T_5$ and $R_8$ is ethyl.

The present disclosure provides the compounds of Formula (VIa):

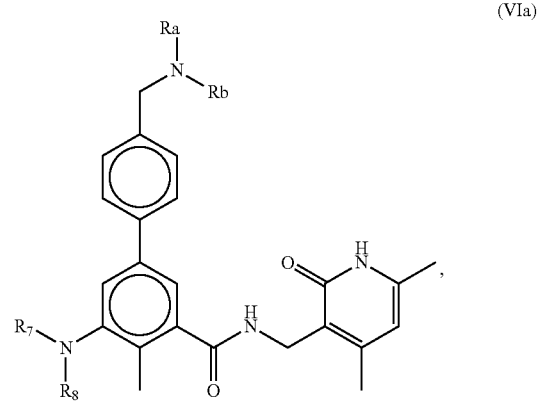

(VIa)

or a pharmaceutically acceptable salts or esters thereof, wherein $R_7$, $R_8$, $R_a$, and $R_b$ are defined herein.

The compounds of Formula (VIa) can include one or more of the following features:

For example, each of $R_a$ and $R_b$ independently is H or $C_1$-$C_6$ alkyl optionally substituted with one or more —$Q_3$—$T_3$.

For example, one of $R_a$ and $R_b$ is H.

For example, $R_a$ and $R_b$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, morpholinyl, 1,4-diazepanyl, 1,4-oxazepanyl, 2-oxa-5-azabicyclo[2.2.1] heptanyl, 2,5-diazabicyclo[2.2.1]heptanyl, and the like) and the ring is optionally substituted with one or more —$Q_3$—$T_3$.

For example, $R_a$ and $R_b$, together with the N atom to which they are attached, form azetidinyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, or morpholinyl, and the ring is optionally substituted with one or more —$Q_3$—$T_3$.

For example, one or more —$Q_3$—$T_3$ are oxo.

For example, $Q_3$ is a bond or unsubstituted or substituted $C_1$-$C_3$ alkyl linker.

For example, $T_3$ is H, halo, 4 to 7-membered heterocycloalkyl, $C_1$-$C_3$ alkyl, $OR_d$, $COOR_d$, —$S(O)_2R_d$, or —$NR_dR_e$.

For example, each of $R_d$ and $R_e$ independently being H or $C_1$-$C_6$ alkyl.

For example, $R_7$ is $C_3$-$C_8$ cycloalkyl or 4 to 7-membered heterocycloalkyl, each optionally substituted with one or more —$Q_5$—$T_5$.

For example, $R_7$ is piperidinyl, tetrahydropyran, tetrahydro-2H-thiopyranyl, cyclopentyl, cyclohexyl, pyrrolidinyl, or cycloheptyl, each optionally substituted with one or more —$Q_5$—$T_5$.

For example, $R_7$ is cyclopentyl cyclohexyl or tetrahydro-2H-thiopyranyl, each of which is optionally substituted with one or more —$Q_5$—$T_5$.

For example, $Q_5$ is NHC(O) and $T_5$ is $C_1$-$C_6$ alkyl or $C_1$-$C_6$ alkoxy, each For example, one or more —$Q_5$—$T_5$ are oxo.

For example, $R_7$ is 1-oxide-tetrahydro-2H-thiopyranyl or 1,1-dioxide-tetrahydro-2H-thiopyranyl.

For example, $Q_5$ is a bond and $T_5$ is amino, mono-$C_1$-$C_6$ alkylamino, di-$C_1$-$C_6$ alkylamino.

For example, $Q_5$ is CO, $S(O)_2$, or NHC(O); and $T_5$ is $C_1$-$C_6$ alkyl, $C_1$-$C_6$ alkoxyl, $C_3$-$C_8$ cycloalkyl, or 4 to 7-membered heterocycloalkyl.

For example, $R_8$ is H or $C_1$-$C_6$ alkyl which is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino.

For example, $R_8$ is H, methyl, or ethyl.

Other compounds of Formulae (I)—(VIa) suitable for the methods of the disclosure are described in U.S. Publications US 20120264734 and US 20140107122, the contents of which are hereby incorporated by reference in their entireties. The compounds of the disclosure are suitable for administration as part of a combination therapy with one or more other therapeutic agents or treatment modality, suitable to be administered together, sequentially, or in alternation.

In some embodiments, the compound suitable for the methods disclosed herein is EPZ-6438 (tazemetostat):

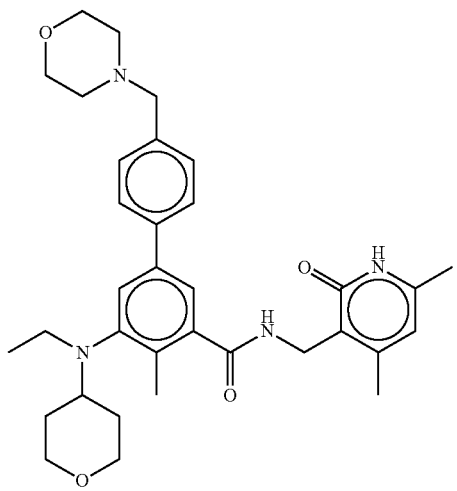

or a pharmaceutically acceptable salt thereof.

EPZ-6438 or a pharmaceutically acceptable salt thereof, as described herein, is potent in targeting both WT and mutant EZH2. EPZ-6438 is orally bioavailable and has high selectivity to EZH2 compared with other histone methyltransferases (i.e. >20,000 fold selectivity by Ki). Importantly, EPZ-6438 has target methyl mark inhibition that results in the killing of genetically defined cancer cells in vitro. Animal models have also shown sustained in vivo efficacy following inhibition of target methyl mark. Clinical trial results described herein also demonstrate the safety and efficacy of EPZ-6438.

In some embodiments, EPZ-6438 or a pharmaceutically acceptable salt thereof is administered to the subject at a dose of approximately 100 mg to approximately 3,200 mg daily, such as about 100 mg BID to about 1,600 mg BID (e.g., 100 mg BID, 200 mg BID, 400 mg BID, 800 mg BID, or 1,600 mg BID), for treating a germinal center-derived lymphoma.

In some embodiments, EPZ-6438 or a pharmaceutically acceptable salt thereof is administered in combination (either simultaneously or sequentially) with a second therapeutic agent, such as one or more components of R—CHOP, a BCL inhibitor, or a BCR inhibitor. The therapeutic agent for the combination therapy, for example, is selected from Alisertib, Dasatinib, Enzastaurin, GDC0068, GSK1070916, GSK2126458, GSK690693, Sorafenib, Vemurafenib, Ruxolitinib, Fedratinib, Tofacitinib, JQ1, Methotrexate, Lenalidomide, OG-L002, and GSK J4; preferably selected from Alisertib, Enzastaurin, Vemurafenib, Dasatinib, GDC0068, GSK1070916, GSK2126458, GSK690693, and JQ1, or preferably selected from GDC0068, GSK1070916, GSK2126458, GSK690693, and JQ1, or preferably selected from Alisertib, Enzastaurin, and Vemurafenib. For example, EPZ-6438 or a pharmaceutically acceptable salt thereof (either referred to as "EPZ-6438" in FIGS. 1-6) has either additive or synergistic effects when combined with drugs that target the BCR/PI3K pathways in cell lines harboring either mutant EZH2, or WT EZH2 germinal center lymphoma cell lines. See, e.g., FIGS. 1 and 3, and Tables 2 and 3. There has been no effect observed in ABC lymphoma cell lines when they are exposed to a combination of EPZ-6438 and drugs that target BCR/PI3K pathways. Importantly, EPZ-6438, combined with a drug that targets the BCR/PI3K pathways, shows a synergistic effect in germinal center B-cell lymphoma (GCB lymphoma) cell lines, regardless of whether the GCB-lymphoma cell lines contained WT or mutant EZH2 protein.

Other embodiments or examples of combination therapy are described in co-pending application, i.e., PCT/US2014/069167, and International Application PCT/US2013/036452 which published as WO 2013/155464, the contents of each of which are hereby incorporated by reference in their entireties.

In some embodiments, a compound (e.g., EZH2 inhibitor) that can be used in any methods presented here is:

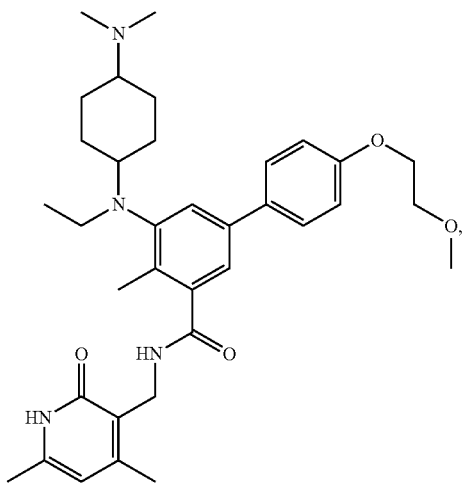
(A)

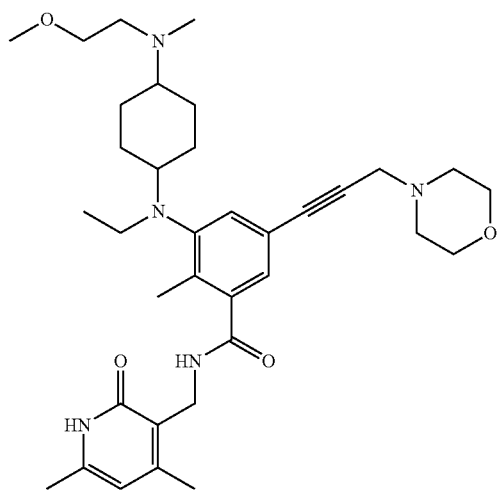
(B)

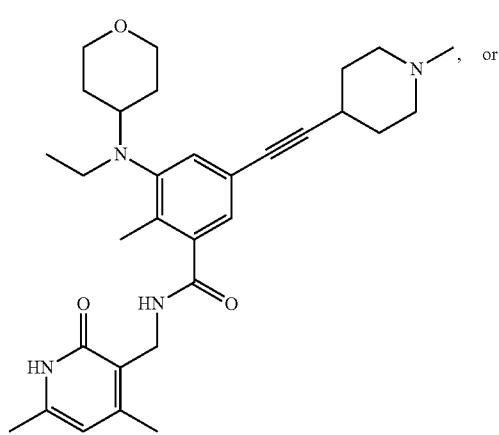
(C) or

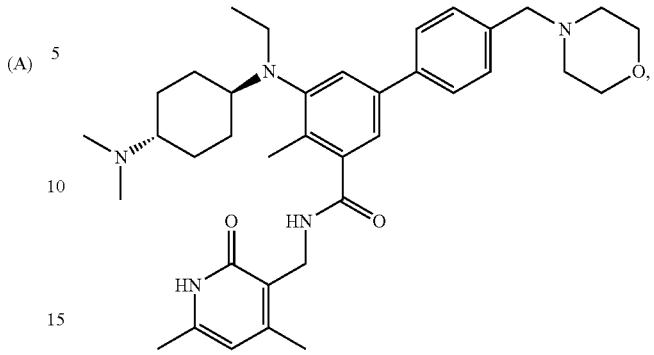
(D)

or stereoisomers thereof or pharmaceutically acceptable salts and solvates thereof.

In certain embodiments, a compound that can be used in any methods presented here is Compound E:

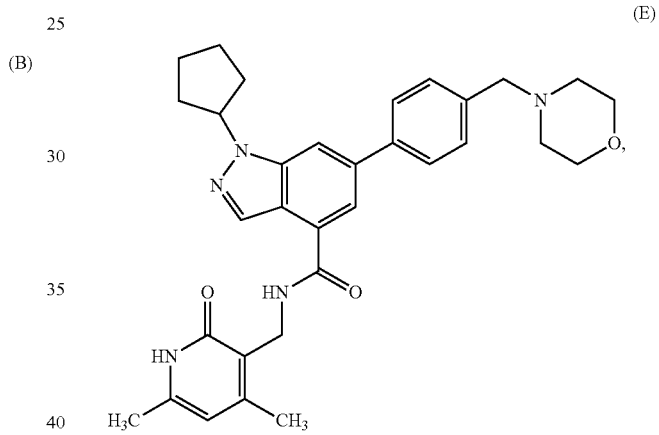
(E)

or pharmaceutically acceptable salts thereof.

In some embodiments, a compound (e.g., EZH2 inhibitor) that can be used in any methods presented here is GSK-126 having the following formula:

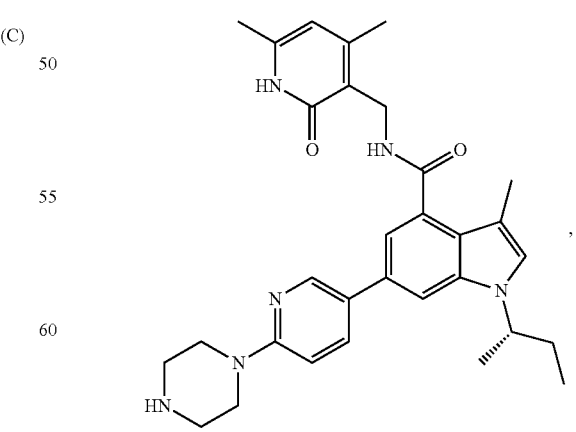

stereoisomers thereof, or pharmaceutically acceptable salts or solvates thereof.

In certain embodiments, a compound that can be used in any methods presented here is Compound F:

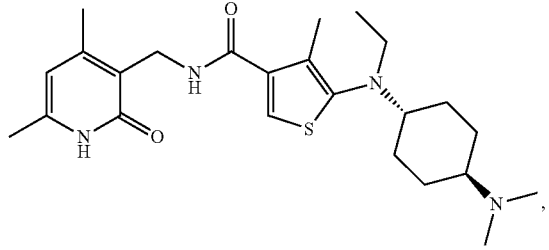

or stereoisomers thereof or pharmaceutically acceptable salts and solvates thereof.

In certain embodiments, a compound (e.g., EZH2 inhibitor) that can be used in any methods presented here is any of Compounds Ga-Gc:

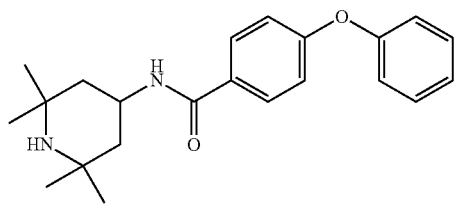

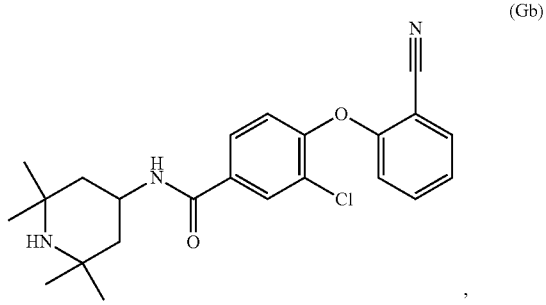

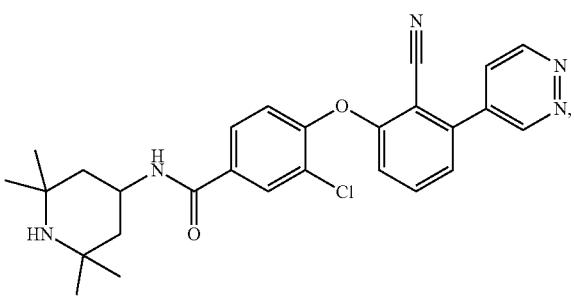

or a stereoisomer, pharmaceutically acceptable salt or solvate thereof.

In certain embodiments, a compound (e.g., EZH2 inhibitor) that can be used in any methods presented here is CPI-1205 or GSK343.

Additional suitable EZH2 inhibitors will be apparent to those skilled in the art. In some embodiments of the strategies, treatment modalities, methods, combinations, and compositions provided herein, the EZH2 inhibitor is an EZH2 inhibitor described in U.S. Pat. No. 8,536,179 (describing GSK-126 among other compounds and corresponding to WO 2011/140324), the entire contents of each of which are incorporated herein by reference.

In some embodiments of the strategies, treatment modalities, methods, combinations, and compositions provided herein, the EZH2 inhibitor is an EZH2 inhibitor described in PCT/US2014/015,706, published as WO 2014/124,418, in PCT/US2013/025,639, published as WO 2013/120,104, and in U.S. Ser. No. 14/839,273, published as US 2015/0368229, the entire contents of each of which are incorporated herein by reference. In some embodiments of the strategies, treatment modalities, methods, combinations, and compositions provided herein, the EZH2 inhibitor is a compound of the formula:

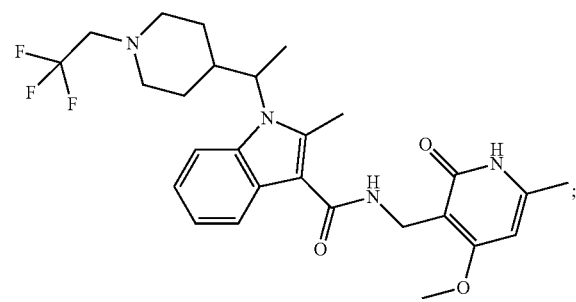 [SMILES: COc1cc(C)[nH]c(=O)c1CNC(=O)c1c(C)n(C(C)C2CCN(CC(F)(F)F)CC2)c2ccccc12]

or a pharmaceutically acceptable salt thereof (see, for example US 2015/0368229, the contents of which are incorporated herein).

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono-or multi-ring (e.g., fused, bridged, or spiro rings) system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydropyranyl, dihydropyranyl, pyranyl, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro

[3.3]heptanyl, 2,6-diazaspiro[3.3]heptanyl, 1,4-dioxa-8-azaspiro[4.5]decanyl and the like.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "alkyl linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2CH_2$—), s-butyl (—$CHCH_3CH_2CH_2$—), i-butyl (—$C(CH_3)_2CH_2$—), n-pentyl (—$CH_2CH_2CH_2CH_2CH_2$—), s-pentyl (—$CHCH_3CH_2CH_2CH_2$—) or n-hexyl (—$CH_2CH_2CH_2CH_2CH_2CH_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethylpiperidinyl and 2,2,6,6-tetramethyl-1,2,3,6-tetrahydropyridinyl.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g. 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and S(O)$_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. Carbocycle includes cycloalkyl and aryl. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In some embodiments, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" or "heterocyclic group" includes any ring structure (saturated, unsaturated, or aromatic) which contains at least one ring heteroatom (e.g., N, O or S). Heterocycle includes heterocycloalkyl and heteroaryl. Examples of heterocycles include, but are not limited to, morpholine, pyrrolidine, tetrahydrothiophene, piperidine, piperazine, oxetane, pyran, tetrahydropyran, azetidine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

The term "hydroxy" or "hydroxyl" includes groups with an —OH or —O⁻.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" includes compounds and moieties which contain a carbon connected with a double bond to an oxygen atom. Examples of moieties containing a carbonyl to include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to unsubstituted or substituted —$NH_2$. "Alkylamino" includes groups of compounds wherein nitrogen of —$NH_2$ is bound to at least one alkyl group. Examples of alkylamino groups include benzylamino, methylamino, ethylamino, phenethylamino, etc. "Dialkylamino" includes groups wherein the nitrogen of —$NH_2$ is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

Compounds of the present disclosure that contain nitrogens can be converted to N-oxides by treatment with an oxidizing agent (e.g., 3-chloroperoxybenzoic acid (mCPBA)

and/or hydrogen peroxides) to afford other compounds suitable for any methods disclosed herein. Thus, all shown and claimed nitrogen-containing compounds are considered, when allowed by valency and structure, to include both the compound as shown and its N-oxide derivative (which can be designated as N→O or N⁺—O⁻). Furthermore, in other instances, the nitrogens in the compounds of the present disclosure can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

"Isomerism" means compounds that have identical molecular formulae but differ in the sequence of bonding of their atoms or in the arrangement of their atoms in space. Isomers that differ in the arrangement of their atoms in space are termed "stereoisomers."

Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It should also be understood that when compounds have chiral isomeric or geometric isomeric forms, all isomeric forms are intended to be included in the scope of the present disclosure, and the naming of the compounds does not exclude any isomeric forms.

Furthermore, the structures and other compounds discussed in this disclosure include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertible by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. An example of keto-enol equilibria is between pyridin-2(1H)-ones and the corresponding pyridin-2-ols, as shown below.

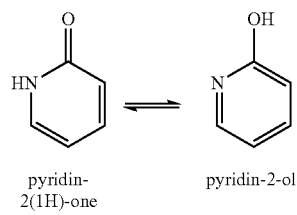 [SMILES: O=c1cccc[nH]1 ; Oc1ccccn1]

pyridin-2(1H)-one    pyridin-2-ol

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form.

The compounds of the present disclosure include the compounds themselves, as well as their salts and their solvates, if applicable. A salt, for example, can be formed between an anion and a positively charged group (e.g., amino) on an aryl- or heteroaryl-substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on an aryl- or heteroaryl-substituted benzene compound. Suitable cations include sodium ion, potassium ion, magnesium ion, calcium ion, and an ammonium cation such as tetramethylammonium ion. The aryl- or heteroaryl-substituted benzene compounds also include those salts containing quaternary nitrogen atoms. In the salt form, it is understood that the ratio of the compound to the cation or anion of the salt can be 1:1, or any ration other than 1:1, e.g., 3:1, 2:1, 1:2, or 1:3.

Additionally, the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (I) are aryl- or heteroaryl-substituted benzene compounds, and have Formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, *Chem. Rev.* 96, 3147-3176, 1996.

The present disclosure is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

In certain embodiments, "combination therapy" is intended to embrace administration of two or more therapeutic agents in a sequential manner, wherein each therapeutic agent is administered at a different time, as well as administration of these therapeutic agents, or at least two of the therapeutic agents concurrently, or in a substantially simultaneous manner. Simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Therapeutic agents may also be administered in alternation.

In certain aspects of the disclosure, the combination therapies featured in the present disclosure can result in a synergistic effect in the treatment of a disease or cancer. A "synergistic effect" is defined as where the efficacy of a combination of therapeutic agents is greater than the sum of the effects of any of the agents given alone. A synergistic effect may also be an effect that cannot be achieved by administration of any of the compounds or other therapeutic agents as single agents. The synergistic effect may include, but is not limited to, an effect of treating cancer by reducing tumor size, inhibiting tumor growth, or increasing survival of the subject. The synergistic effect may also include reducing cancer cell viability, inducing cancer cell death, and inhibiting or delaying cancer cell growth.

In certain aspects of the disclosure "combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

In another aspect, a composition of the present disclosure, or a pharmaceutically acceptable salt, solvate, analog or derivative thereof, may be administered in combination with radiation therapy. Radiation therapy can also be administered in combination with a composition of the present disclosure and another chemotherapeutic agent described herein as part of a multiple agent therapy.

Combination therapy can be achieved by administering two or more agents, e.g., EPZ-6438 and one or more other therapeutic agents, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

The present disclosure also provides pharmaceutical compositions comprising a compound of the disclosure or pharmaceutically acceptable salts thereof, and one or more other therapeutic agents disclosed herein, mixed with pharmaceutically suitable carriers or excipient(s) at doses to treat or prevent a disease or condition as described herein. In one aspect, the present disclosure also provides pharmaceutical compositions comprising any compound of the present disclosure or pharmaceutically acceptable salts thereof, and one or more therapeutic agents, mixed with pharmaceutically suitable carriers or excipient (s) at doses to treat or prevent a disease or condition as described herein. In another aspect, the present disclosure also provides pharmaceutical compositions comprising EPZ-6438

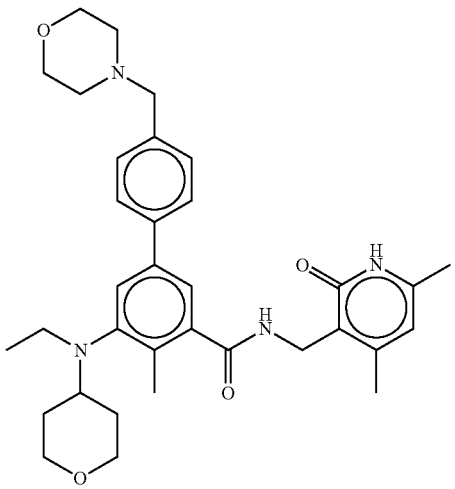

or pharmaceutically acceptable salts thereof, and one or more therapeutic agents, mixed with pharmaceutically suitable carriers or excipient(s) at doses to treat or prevent a disease or condition as described herein. The pharmaceutical compositions of the present disclosure can also be administered in combination with other therapeutic agents or therapeutic modalities simultaneously, sequentially, or in alternation.

In some embodiments, a pharmaceutical composition of EPZ-6438 is administered simultaneously with a pharmaceutical composition of another therapeutic agent that is selected from Alisertib, Dasatinib, Enzastaurin, GDC0068, GSK1070916, GSK2126458, GSK690693, Sorafenib, Vemurafenib, Ruxolitinib, Fedratinib, Tofacitinib, JQ1, Methotrexate, Lenalidomide, OG-L002, and GSK J4 (preferably selected from Dasatinib, GDC0068, GSK1070916, GSK2126458, GSK690693, and JQ1, or preferably selected from GDC0068, GSK1070916, GSK2126458, GSK690693, and JQ1). In another embodiment, a pharmaceutical composition of EPZ-6438 is administered prior to administration of a combination of EPZ-6438 with another therapeutic agent that is selected from Alisertib, Dasatinib, Enzastaurin, GDC0068, GSK1070916, GSK2126458, GSK690693, Sorafenib, Vemurafenib, Ruxolitinib, Fedratinib, Tofacitinib, JQ1, Methotrexate, Lenalidomide, OG-L002, and GSK J4 (preferably selected from Dasatinib, GDC0068, GSK1070916, GSK2126458, GSK690693, and JQ1 or preferably selected from GDC0068, GSK1070916, GSK2126458, GSK690693, and JQ1). In yet another embodiment, a pharmaceutical composition of EPZ-6438 is administered subsequent to administration of a combination of EPZ-6438 with another therapeutic agent that is selected from Alisertib, Dasatinib, Enzastaurin, GDC0068, GSK1070916, GSK2126458, GSK690693, Sorafenib, Vemurafenib, Ruxolitinib, Fedratinib, Tofacitinib, JQ1, Methotrexate, Lenalidomide, OG-L002, and GSK J4 (preferably selected from Dasatinib, GDC0068, GSK1070916, GSK2126458, GSK690693, and JQ1 or preferably selected from GDC0068, GSK1070916, GSK2126458, GSK690693, and JQ1).

A "pharmaceutical composition" is a formulation containing the compound of the present disclosure in a form suitable for administration to a subject. A compound of the present disclosure and one or more other therapeutic agents described herein each can be formulated individually or in multiple pharmaceutical compositions in any combinations of the active ingredients. Accordingly, one or more administration routes can be properly elected based on the dosage form of each pharmaceutical composition. Alternatively, a compound of the present disclosure and one or more other therapeutic agents described herein can be formulated as one pharmaceutical composition.

In some embodiments, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In some embodiments, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfate; chelating agents such as ethylenediaminetetraacetic acid;

buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A composition of the present disclosure can be administered to a subject in many of the well-known methods currently used for chemotherapeutic treatment. For example, for treatment of cancers, a compound of the present disclosure may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. For example, the therapeutically effective amount of an EZH2 inhibitor can be different for a patient having an EZH2 wild type germinal center B-cell lymphoma than for a patient having an EZH2 mutant germinal center B-cell lymphoma. Therapeutically effective amounts for a given situation can be determined by routine experimentation that is within the skill and judgment of the clinician.

In certain embodiments the therapeutically effective amount of each pharmaceutical agent used in combination will be lower when used in combination in comparison to monotherapy with each agent alone. Such lower therapeutically effective amount could afford for lower toxicity of the therapeutic regimen.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the EZH2 inhibitor compounds described herein, other therapeutic agents described herein, compositions comprising a compound of the disclosure and one or more other therapeutic agents, or the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The composition of the present disclosure is capable of further forming salts. The composition of the present disclosure is capable of forming more than one salt per molecule, e.g., mono-, di-, tri-. All of these forms are also contemplated within the scope of the disclosure.

As used herein, "pharmaceutically acceptable salts" refer to derivatives of the compounds of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates), of the same salt.

The composition of the present disclosure may also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The composition, or pharmaceutically acceptable salts or solvates thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In some embodiments, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

As used herein, a "subject in need thereof" is a subject having a germinal center-derived lymphoma, or a subject having an increased risk of developing such disorder relative to the population at large. A subject in need thereof can have a precancerous condition. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

The subject of the present disclosure includes any human subject who has been diagnosed with, has symptoms of, or is at risk of developing a germinal center-derived lymphoma. The subject of the present disclosure includes any human subject expressing a mutant EZH2 or WT EZH2 or has a mutation in the EZH2 gene or has a wild-type EZH2 gene. For example, a mutant EZH2 comprises one or more mutations, wherein the mutation is a substitution, a point mutation, a nonsense mutation, a missense mutation, a deletion, or an insertion or any other EZH2 mutation described herein.

The subject of the present disclosure also includes any human subject who has been diagnosed with, has symptoms of, or is at risk of developing PMBCL. The subject of the present disclosure includes any human subject expressing a mutant EZH2 or WT EZH2 or has a mutation in the EZH2 gene or has a wild-type EZH2 gene. For example, a mutant EZH2 comprises one or more mutations, wherein the mutation is a substitution, a point mutation, a nonsense mutation, a missense mutation, a deletion, or an insertion or any other EZH2 mutation described herein.

A subject in need thereof may have refractory or resistant cancer. "Refractory or resistant cancer" means cancer that does not respond to treatment. The cancer may be resistant at the beginning of treatment or it may become resistant during treatment. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy. In certain embodiments the prior therapy is monotherapy. In certain embodiments the prior therapy is combination therapy.

In some embodiments, a subject in need thereof may have a secondary cancer as a result of a previous therapy. "Secondary cancer" means cancer that arises due to or as a result from previous carcinogenic therapies, such as chemotherapy.

The subject may also exhibit resistance to EZH2 histone methyltransferase inhibitors or any other therapeutic agent.

The disclosure also features a method of selecting a therapy for a subject having a germinal center-derived lymphoma or having Primary Mediastinal Large B-Cell Lymphoma (PMBCL). The method includes the steps of: detecting the presence or absence of one or more EZH2 mutations described herein in a sample from the subject; and selecting, based on the presence or absence of the one or more EZH2 mutations, a therapy for treating the germinal center-derived lymphoma or for treating the PMBCL. In some embodiments, the therapy includes administering to the subject a therapeutically effective amount of an EZH2 inhibitor described herein. In some embodiments, the method further includes administrating to the subject a therapeutically effective amount of a second therapeutic agent. An EZH2 mutation or absence thereof can be detected using any suitable method known in the art. The methods and uses described herein may include steps of detecting the presence or absence of one or more EZH2 mutations described herein in a sample from a subject in need thereof prior to and/or after the administration of a composition of the disclosure (e.g., a composition comprising a compound of the present disclosure or pharmaceutically acceptable salts thereof, alone or in combination with one or more second therapeutic agents) to the subject.

The present disclosure provides personalized medicine, treatment and/or cancer management for a subject having or at risk of having a germinal center-derived lymphoma, by genetic screening of one or more EZH2 mutations described herein in the subject. For example, the present disclosure provides methods for treating or alleviating a symptom of a germinal center-derived lymphoma in a subject in need thereof by determining responsiveness of the subject to a therapy and when the subject is responsive to the therapy, administering to the subject a composition of the disclosure. Once the responsiveness of a subject is determined, a therapeutically effective amount of a composition, for example, a composition comprising a compound of the present disclosure or pharmaceutically acceptable salts thereof, alone or in combination with one or more second therapeutic agents, can be administered. The therapeutically effective amount of a composition can be determined by one of ordinary skill in the art.

As used herein, the term "responsiveness" is interchangeable with terms "responsive", "sensitive", and "sensitivity", and it is meant that a subject is showing therapeutic responses when administered a composition of the disclosure, e.g., tumor cells or tumor tissues of the subject undergo apoptosis and/or necrosis, and/or display reduced growing, dividing, or proliferation. This term is also meant that a subject will or has a higher probability, relative to the population at large, of showing therapeutic responses when administered a composition of the disclosure, e.g., tumor cells or tumor tissues of the subject undergo apoptosis and/or necrosis, and/or display reduced growing, dividing, or proliferation.

By "sample" it means any biological sample derived from the subject, includes but is not limited to, cells, tissues samples, body fluids (including, but not limited to, mucus, blood, plasma, serum, urine, saliva, and semen), tumor cells, and tumor tissues. Preferably, the sample is selected from bone marrow, peripheral blood cells, blood, plasma and serum. Samples can be provided by the subject under treatment or testing. Alternatively samples can be obtained by the physician according to routine practice in the art.

As used herein, "candidate compound" refers to a compound of the present disclosure, or a pharmaceutically acceptable salt or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present disclosure, or a pharmaceutically acceptable salt or solvate thereof. The biological or medical response can be the treatment of cancer. The biological or medical response can be treatment or prevention of a cell proliferative disorder. In vitro or in vivo biological assays can include, but are not limited to, enzymatic activity assays, electrophoretic mobility shift assays, reporter gene assays, in vitro cell viability assays, and the assays described herein.

As used herein, "treating" or "treat" describes the management and care of a patient for the purpose of combating a disease, condition, or disorder and includes the administration of a compound of the present disclosure, or a pharmaceutically acceptable salt or solvate thereof, to alleviate the symptoms or complications of a disease, condition or disorder, or to eliminate the disease, condition or disorder.

A composition of the present disclosure, or a pharmaceutically acceptable salt or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the disclosure leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the disclosure, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present disclosure, or a pharmaceutically acceptable salt, solvate, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present disclosure, or a pharmaceutically acceptable salt, solvate, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, a compound of the present disclosure, or a pharmaceutically acceptable salt or solvate thereof, acts selectively on a cancer or precancerous cell but not on a normal cell. Preferably, a compound of the present disclosure, or a pharmaceutically acceptable salt or solvate thereof, acts selectively to modulate one molecular target (e.g., a target protein methyltransferase) but does not significantly modulate another molecular target (e.g., a non-target protein methyltransferase). The disclosure also provides a method for selectively inhibiting the activity of an enzyme, such as a protein methyltransferase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A composition of the present disclosure, e.g., a composition comprising any compound of the present disclosure or pharmaceutically acceptable salt thereof, and one or more other therapeutic agents, such as prednisone, can modulate the activity of a molecular target (e.g., a target protein methyltransferase). Modulating refers to stimulating or inhibiting an activity of a molecular target. Preferably, a compound of the present disclosure, or a pharmaceutically acceptable salt or solvate thereof, modulates the activity of a molecular target if it stimulates or inhibits the activity of the molecular target by at least 2-fold relative to the activity of the molecular target under the same conditions but lacking only the presence of said compound. More preferably, a compound of the present disclosure, or a pharmaceutically acceptable salt or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A composition of the present disclosure does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a protein methyltransferase isozyme alpha in comparison to a protein methyltransferase isozyme beta). Preferably, a compound of the present disclosure, or a pharmaceutically acceptable salt or solvate thereof, demonstrates a minimum of a fourfold differential, preferably a tenfold differential, more preferably a fifty fold differential, in the dosage required to achieve a biological effect. Preferably, a compound of the present disclosure, or a pharmaceutically acceptable salt or solvate thereof, demonstrates this differential across the range of inhibition, and the differential is exemplified at the $IC_{50}$, i.e., a 50% inhibition, for a molecular target of interest.

Administering a composition of the present disclosure to a cell or a subject in need thereof can result in modulation (i.e., stimulation or inhibition) of an activity of a protein methyltransferase of interest.

Administering a compound of the present disclosure, e.g., a composition comprising any compound of the present disclosure or pharmaceutically acceptable salt thereof, and one or more other therapeutic agents, such as prednisone, to a cell or a subject in need thereof results in modulation (i.e., stimulation or inhibition) of an activity of an intracellular target (e.g., substrate). Several intracellular targets can be modulated with the compounds of the present disclosure, including, but not limited to, protein methyltrasferase.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*, 100(5): 2674-8, 2003. In an aspect, cell death occurs by apoptosis.

Preferably, an effective amount of a composition of the present disclosure, or a pharmaceutically acceptable salt or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a composition of the present disclosure, or a pharmaceutically acceptable salt or solvate thereof, can induce or activate cell death selectively in cancer cells. Contacting a cell with a composition of the present disclosure, or a pharmaceutically acceptable salt or solvate thereof, can induce cell death selectively in one or more cells affected by a cell proliferative disorder. Preferably, administering to a subject in need thereof a composition of the present disclosure, or a pharmaceutically acceptable salt or solvate thereof, induces cell death selectively in one or more cells affected by a cell proliferative disorder.

The present disclosure relates to a method of treating or preventing cancer by administering a composition of the present disclosure, or a pharmaceutically acceptable salt or solvate thereof, to a subject in need thereof, where administration of the composition of the present disclosure, or a pharmaceutically acceptable salt or solvate thereof, results in one or more of the following: prevention of cancer cell proliferation by accumulation of cells in one or more phases of the cell cycle (e.g. G1, G1/S, G2/M), or induction of cell senescence, or promotion of tumor cell differentiation; promotion of cell death in cancer cells via cytotoxicity, necrosis or apoptosis, without a significant amount of cell death in normal cells, antitumor activity in animals with a therapeutic index of at least 2. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), Remington's Pharmaceutical Sciences, Mack Publishing Co., Easton, Pa., $18^{th}$ edition (1990). These texts can, of course, also be referred to in making or using an aspect of the disclosure.

EXAMPLE

Combination Study of EPZ-6438 and Other Therapeutic Agents

The EZH2 inhibitor tazemetostat (EPZ-6438) is currently being evaluated in Phase II clinical trials for the treatment of non-Hodgkin's Lymphoma (NHL). EZH2 inhibitors have shown anti-proliferative effects in multiple pre-clinical models of NHL, and phase I studies of tazemetostat have reported objective clinical responses in patients with B-cell lymphomas. In preclinical models, lymphomas bearing gain-of-function mutations in EZH2 were consistently more sensitive to EZH2 inhibition than were lymphomas with wild type (wt) EZH2. However, recent phase I data have demonstrated that objective responses occur in lymphoma patients with both wt and mutant EZH2. This finding is consistent with reports in the literature that demonstrate a role for EZH2 in maintaining the germinal center phenotype of normal B-cells, as well as regulating the differentiation of both wt and mutant EZH2 B-cell lymphoma cell lines. To understand better the relationship between B-cell maturation and EZH2, we evaluated apoptosis and differentiation in wt and mutant EZH2 DLBCL cell lines. We discovered that cells with mutant EZH2 undergo apoptosis following tazemetostat treatment. In contrast, cell lines with wild-type EZH2 exhibit decreased growth rates and induce PRDM1, a key transcriptional repressor involved in plasma cell differentiation. To explore further these phenomena, we evaluated apoptosis in cells co-treated with tazemetostat and inhibitors or activators of primary B-cell signaling pathways. We discovered that combinations of tazemetostat with inhibitors of B-cell activation, like ibrutinib or corticosteroids, demonstrate synergy in both wt and mutant EZH2 cell lines. Moreover, it was determined that when combined with ibrutinib, tazemetostat induces apoptosis in wt cell lines. It was also discovered that addition of recombinant CD40L, a B-cell co-stimulatory molecule can prevent apoptosis and drive lymphoma cells more towards differentiation. These findings demonstrate that EZH2 inhibition drives lymphoma cells towards cell fate decisions and suggests that an important component of tazemetostat's mechanism of action is to force lymphoma cells to proceed through the normal processes of apoptosis and terminal differentiation.

EZH2 inhibitors are emerging as valuable therapeutic agents for the treatment of non-Hodgkin's lymphoma. The mechanism by which EZH2 inhibitors inhibit lymphoma cell proliferation is an area of active research. EZH2 is known to be a regulator of B-cell maturation and germinal center formation. EZH2 inhibition induces differentiation markers in cell lines derived from multiple lymphoma sub-types. Some of the results presented here indicate that EZH2's role in B-cell maturation contributes to the anti-lymphoma activity of tazemetostat.

FIG. 1. A) 14 evaluable NHL patients treated (V. Ribrag ASH 2015): 13 WT+1 mutant by cobas® EZH2 Mutation Test (in development, Roche Molecular Systems, Inc.) *Cheson Criteria. B) EZH2 mutant cell lines are more sensitive to TAZ in vitro. C) Sensitivity of WT DLBCL cell lines to TAZ does not depend on cell of origin. Cell of origin of cell lines determined by RNAseq analysis (Scott et al. Blood 2014). D) OCI-LY19 and SU-DHL-5 cell line xenograft models show tumor growth inhibition in response to TAZ treatment.

Figure 2:
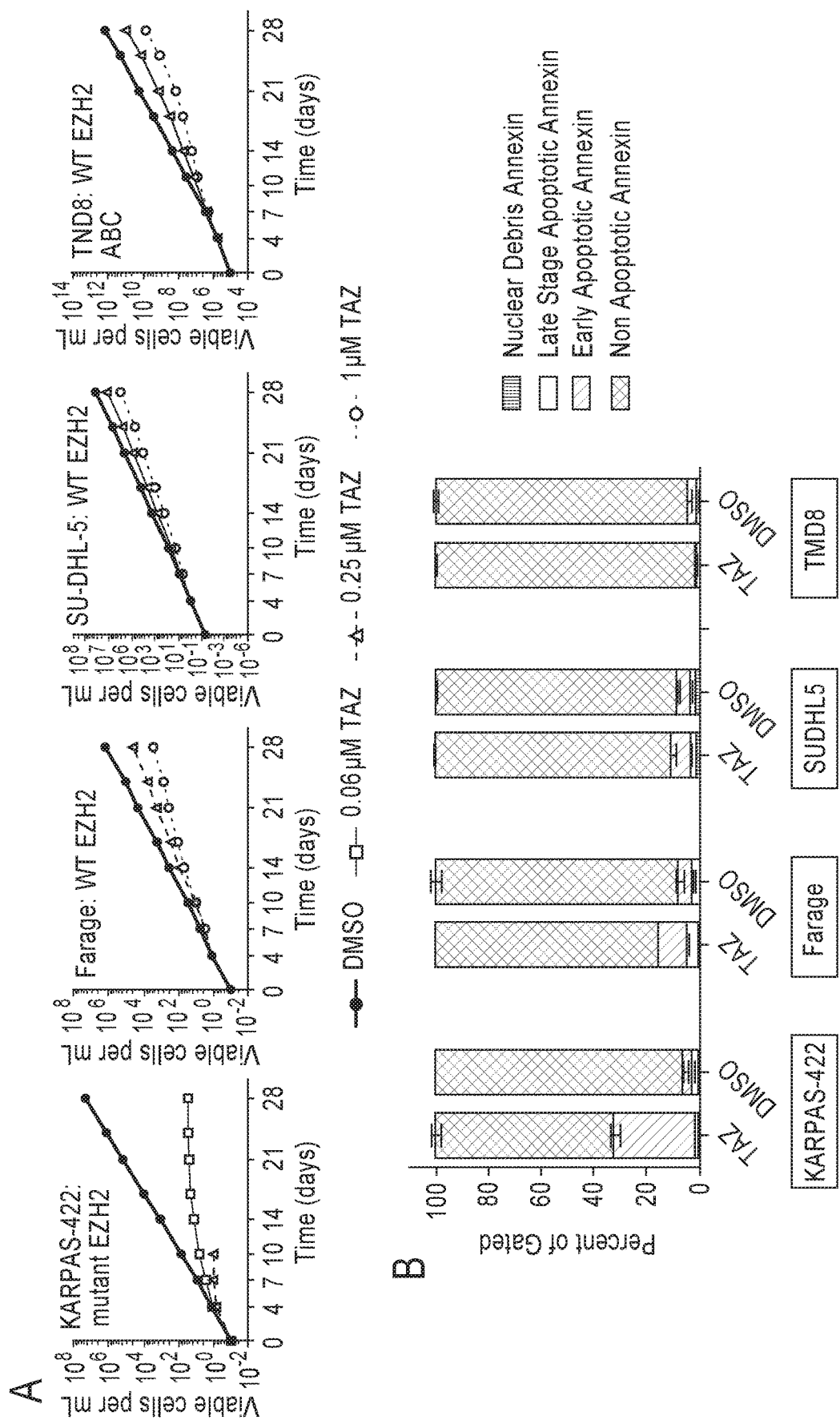
FIG. 2. Varying degrees of anti-proliferative responses can be seen in mutant vs. wt cell lines. A) Cells were treated with TAZ and proliferation was measured by cell counts at the indicated time points. The viable cell count (y axis) in each panel is presented on a logarithmic scale. B) Cells were treated for 10 days with 1 µM TAZ or DMSO. Green stacks represent percentages of cells in early stage apoptosis.

FIG. 2. Varying degrees of anti-proliferative responses can be seen in mutant vs. wt cell lines. A) Cells were treated with TAZ and proliferation was measured by cell counts at the indicated time points. The viable cell count (y axis) in each panel is presented on a logarithmic scale. B) Cells were treated for 10 days with 1 μM TAZ or DMSO. Green stacks represent percentages of cells in early stage apoptosis.

Figure 3:
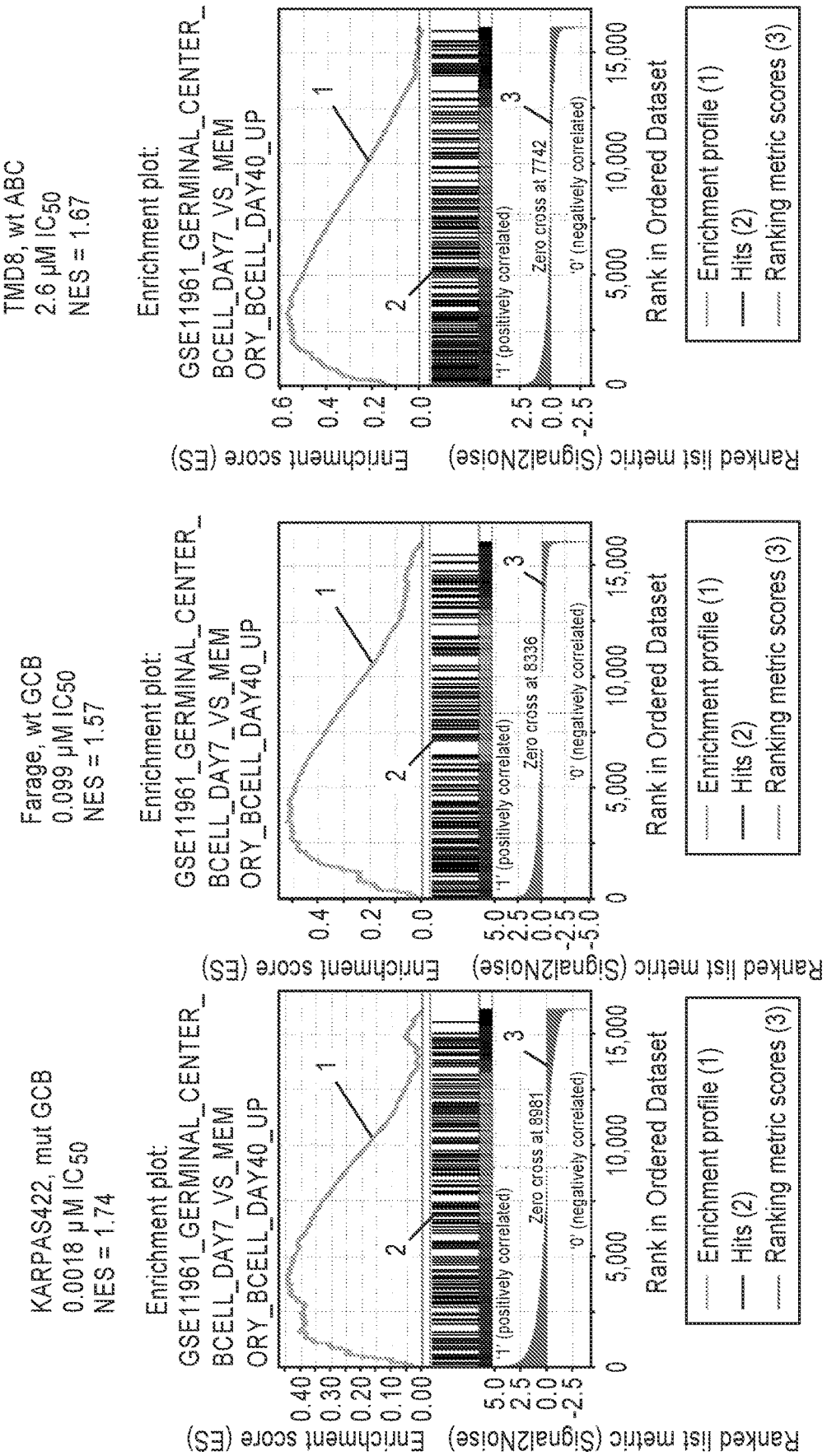
FIG. 3. EZH2 inhibition induces memory cell gene sets in cell lines with both wild type and mutant EZH2.
Figure 3:
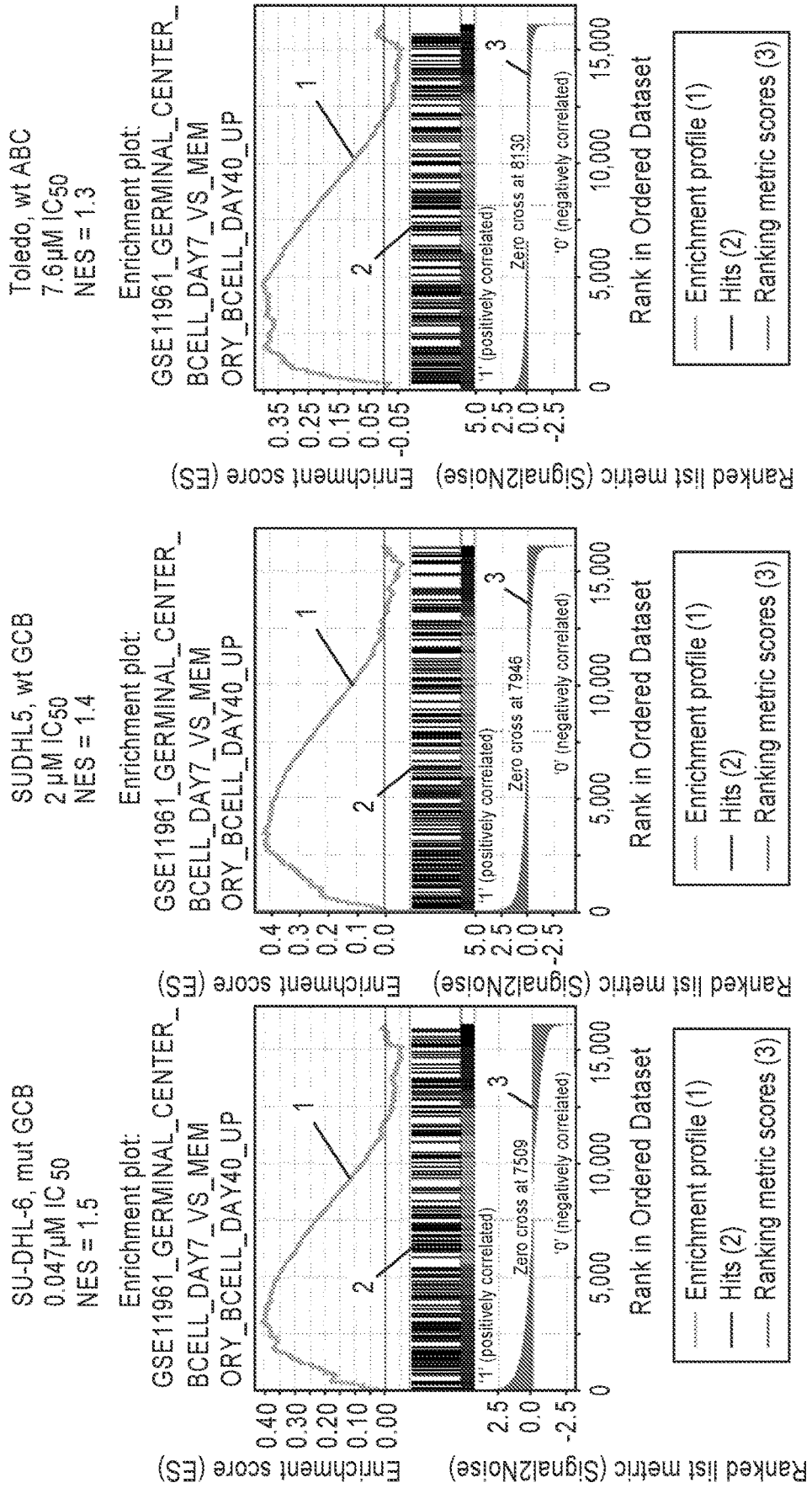

FIG. 3. EZH2 inhibition induces a gene set that is heavily enriched for plasma cell and memory cell genes in DLBCL cell lines. RNAseq data from KARPAS-422 (EZH2 mutant GCB), SU-DHL-6 (EZH2 mutant GCB) Farage (EZH2 wt GCB), SU-DHL-5 (EZH2 wt GCB), TMD8 (EZH2 wt ABC) and Toledo (EZH2 wt ABC) treated with 1 μM TAZ for 4 days was analyzed using GSEA (Broad Institute) for the presence of plasma and memory cell gene sets.

Figure 4:
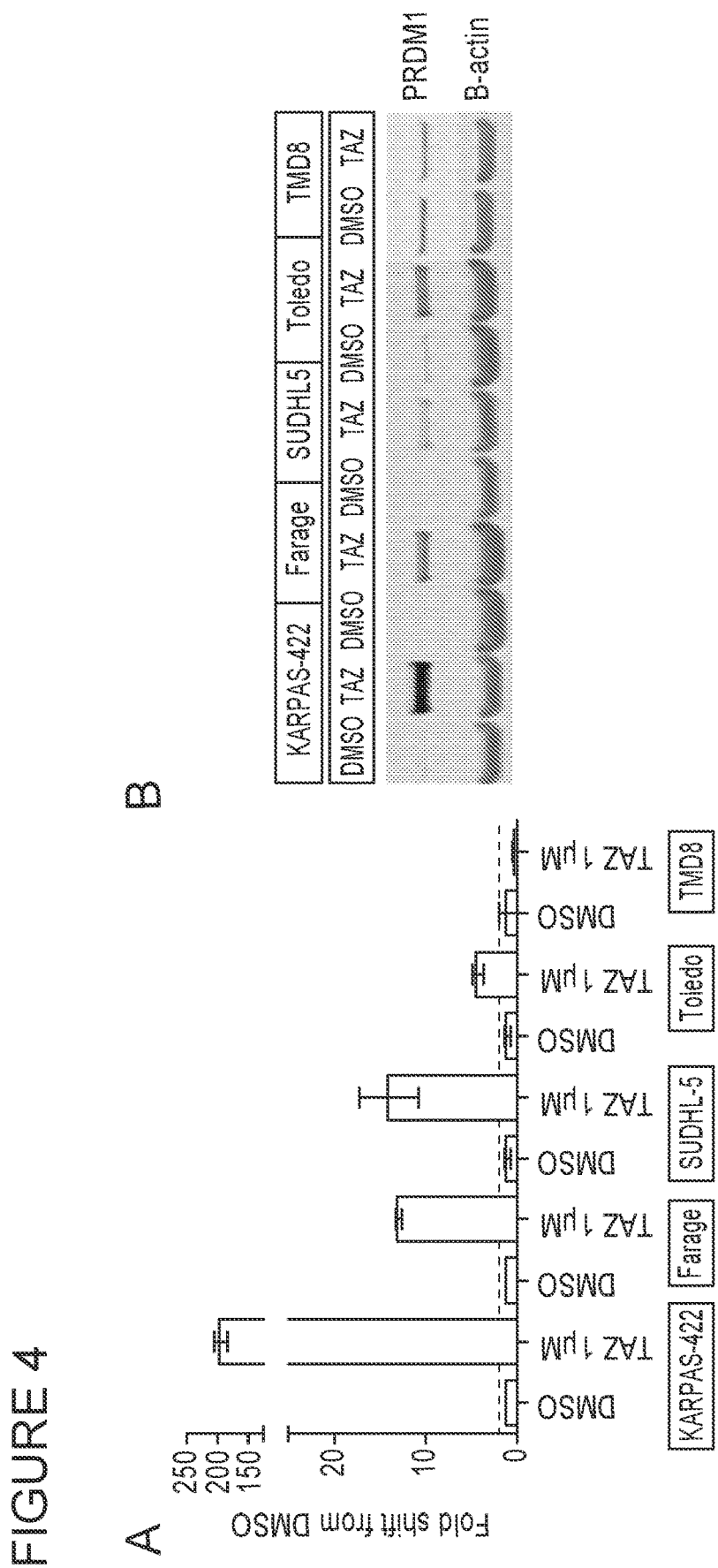
FIG. 4. TAZ induces PRDM1 independently of EZH2 mutational status or TAZ sensitivity.

FIG. 4. Cells were treated for 7 days with 1 μM TAZ or DMSO. All GCB lines show an increase of PRDM1 (BLIMP1) expression by qPCR (A) or western blot (B), while the ABC cell line, TMD8, shows a slight decrease.

As shown in Table 1, combination studies revealed a relationship between B-cell activation and EZH2 inhibition. Synergy was assessed by IC50 shifts or Calcusyn.

TABLE 1

| | Drug Name | Mutant EZH2 GCB | | | | WT EZH2 GCB | | | | | WT EZH2 ABC | | | |
|---|---|---|---|---|---|---|---|---|---|---|---|---|---|---|
| | | WSU-DLCL2 | KAR-PAS-422 | ˜SU-DHL-10 | SU-DHL-6 | OCI-LY19 | HT | #Farage | OCI-LY7 | SU-DHL5 | Toledo | TMD8 | OCI-LY3 | SU-DHL2 |
| | IC$_{50}$ Taz 7d/14d | 100 nM/ 86 nM | 50 nM/ 18 nM | 50 nM/ 58 nM | 100 nM/ 47 nM | 1 μM/ 6.2 μM | 500 nM/ 140 nM | 1 μM/ 99 nM | 1.5 μM/ 1.4 μM | 3.8 μM/ 2.1 μM | >10 μM/ 7.6 μM | 5.5 μM/ 2.6 μM | 5.1 μM/ 820 μM | 1.3 μM/ 230 μM |
| GRAG | Prednisolone | A | A | A | A | A | C | A | A | A | C | A | A | A |
| | Dexamethasone | A | A | A | A | A | C | A | A | A | C | A | A | A |
| B-cell Receptor Pathway | Everolimus | A | B | A | A | C | A | A | A | A | C | A | A | A |
| | Trametinib | A | A | A | A | C | C | A | A | A | C | A | A | C |
| | MK-2206 | A | A | A | A | A | A | A | A | A | C | A | A | C |
| | Ibrutinib | A | A | A | A | C | A | A | A | A | C | A | B | B |
| | Idelalisib | A | A | A | A | C | A | A | A | A | C | A | A | C |
| | Tamatinib | A | A | A | A | C | A | A | A | A | C | A | A | A |
| B-cell Activators | CD40L | D | D | D | D | C | D | C | D | D | A | A | C | D |
| | LPS | D | C | C | C | C | C | C | D | D | A | D | C | C |
| | BAFF | D | C | C | D | C | D | C | C | D | C | D | C | C |
| | APRIL | D | C | C | D | C | C | C | C | D | C | D | C | E |
| | Anti-IgM/IgG | D | D | C | A | C | C | C | C | C | C | A | C | C |

| Synergy or Enhancement | Additivity* | No Effect* | Antagonistic | Not Tested |
|---|---|---|---|---|
| A | B | C | D | E |

Figure 5:
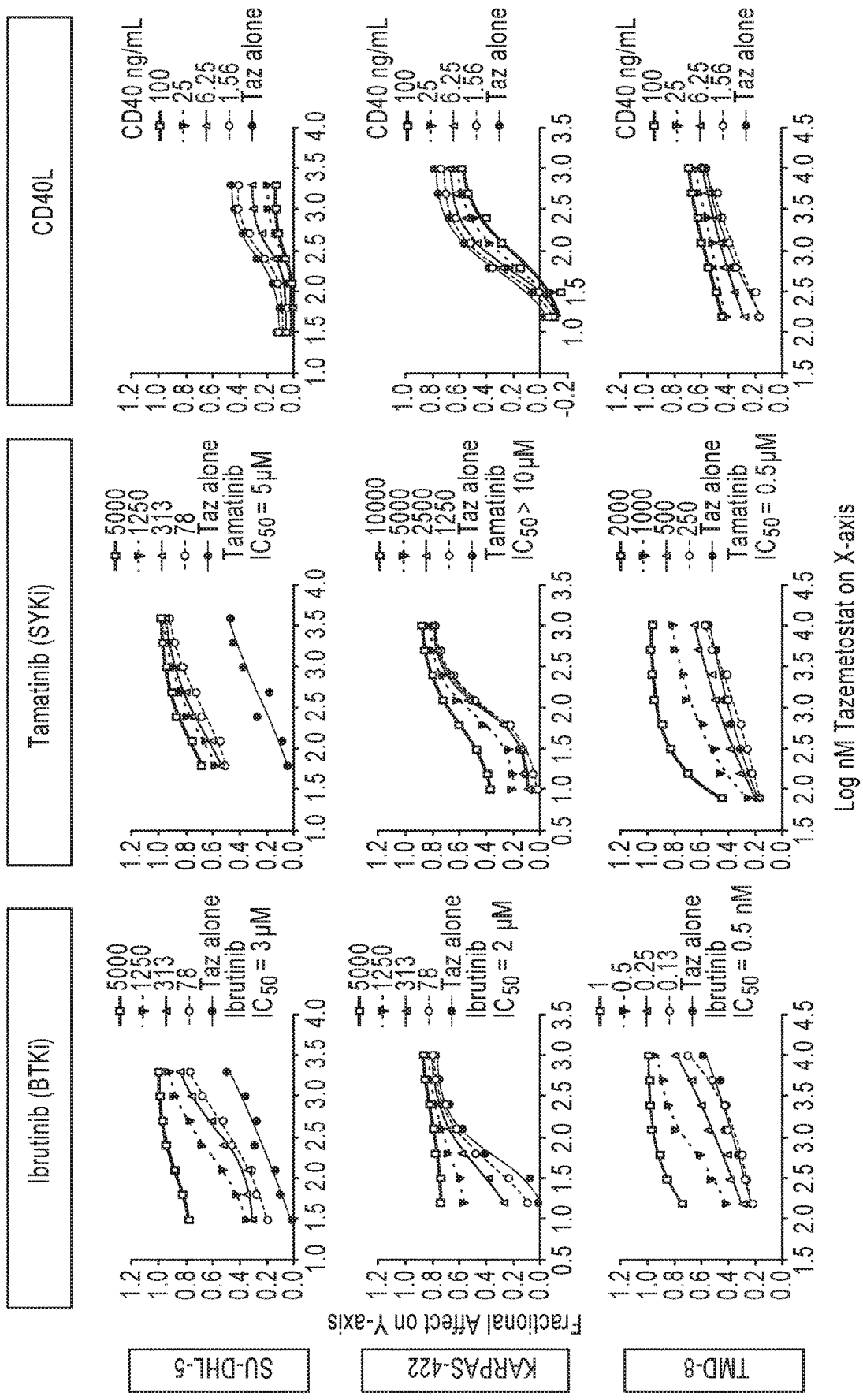
FIG. 5. Tazemetostat makes lymphoma cell lines dependent on activation signals.

*Additivity = when other agent has a single agent effect but causes no enhancement of 6438 effect
No Effect = when other agent has no single agent effect and causes no enhancement of 6438 effect
˜Tested in 4-day cotreatment model
Tested in a 10 or 11 day assay with 7 days pretreatment 3 days or 4 days cotreatment FIG. 5. Synergy is seen with TAZ when combined with ibrutinib or tamatinib in SU-DHL-5 (EZH2 wt), KARPAS-422 (EZH2 mutant) and TMD8 (ABC) cell lines. CD40L combination with TAZ shows antagonism in GCB lines but slight synergy in TMD8

Figure 6:
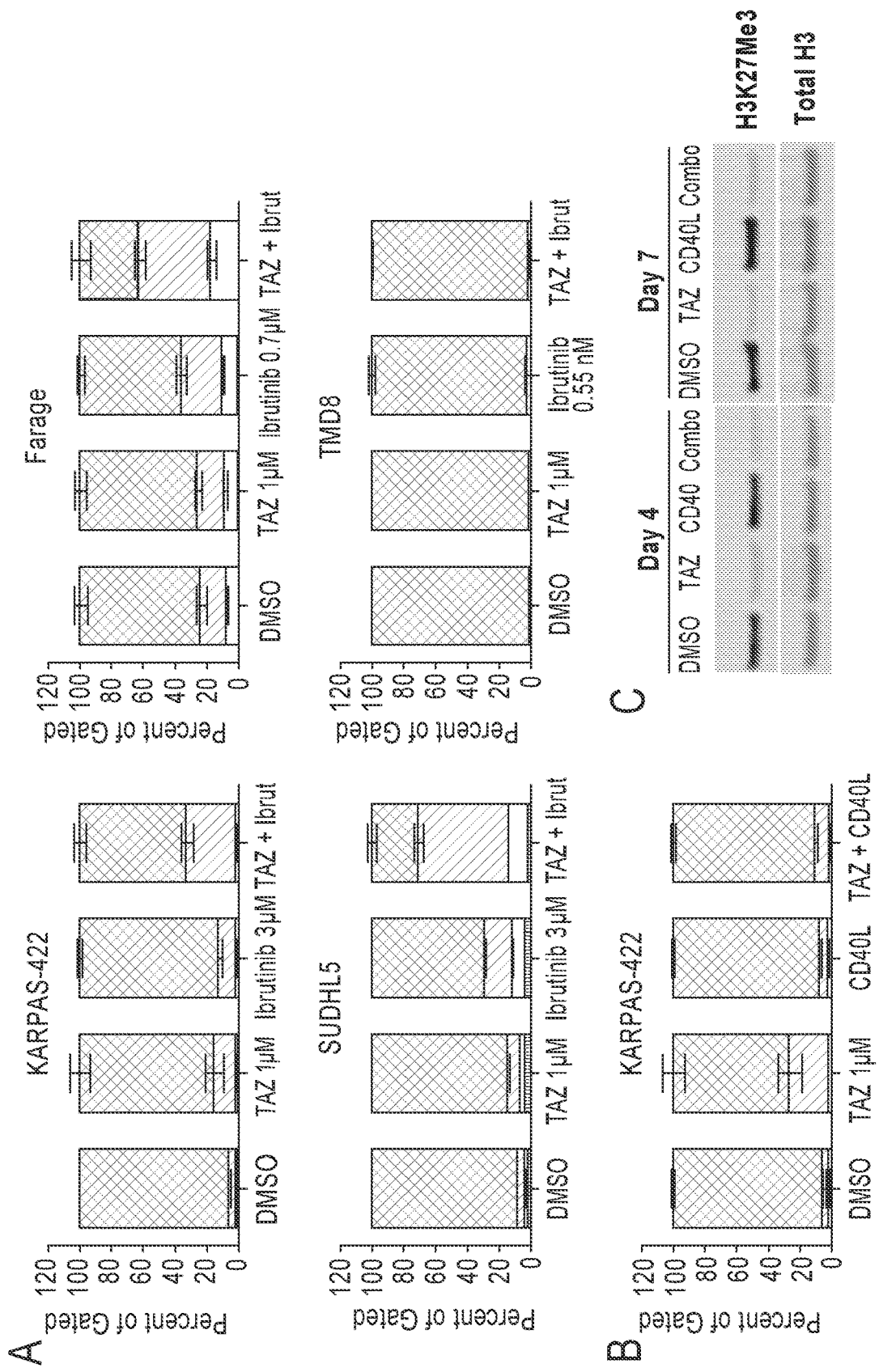
FIG. 6. Inhibitors of B-cell activation transform TAZ induced growth inhibitory phenotype to apoptosis.

FIG. 6. A) Cells were treated for 7 days with single agents or in combination. In the GCB cell lines, a significant increase of apoptosis is seen with the combination of TAZ and ibrutinib compared to the single agents. This effect is not seen in the ABC cell line, TMD8. B) Cells were treated for 10 days with single agents (100 ng/mL CD40L) or in combination. A significant increase of apoptosis is seen with single agent TAZ compared to DMSO and a significant decrease of apoptosis is seen with the combination of TAZ and CD40L compared to TAZ single agent treatment. C) CD40L does not affect TAZ inhibition of H3K27 trimethylation in the KARPAS-422, a mutant EZH2 cell line.

Figure 7:
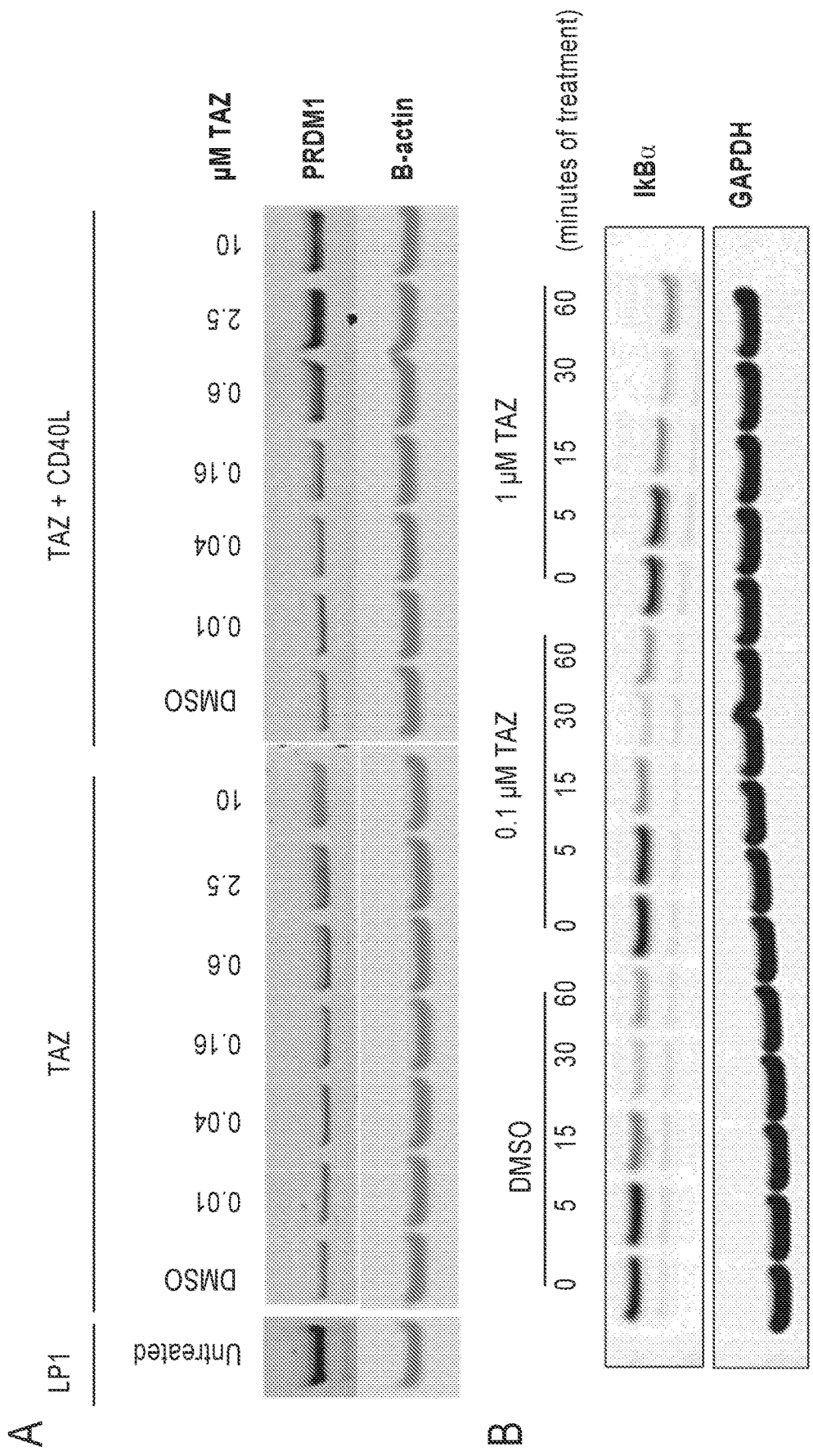
FIG. 7. EZH2 inhibition is required for CD40L induction of PRDM1 in SUDHL-5.
Figure 9:
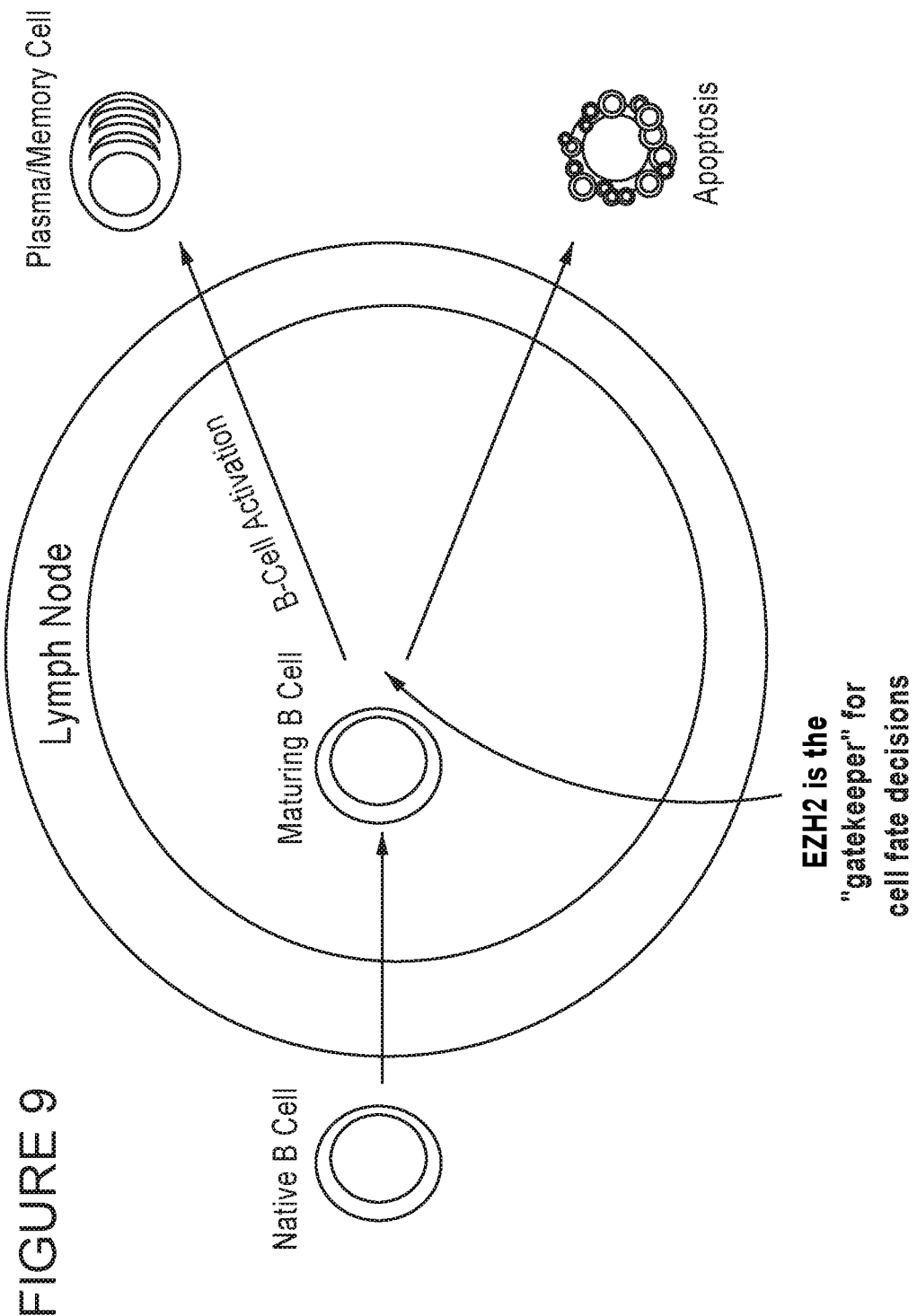
FIG. 9. Schematic demonstrating that EZH2 is a "gate-keeper" for cell fate decisions.

FIG. 7. EZH2 represses CD40L-induced PRDM1 expression A) 14-day co-treatment of SU-DHL-5 (wt EZH2) with TAZ and CD40L leads to up-regulation of PRDM1 B) 4-day treatment in SU-DHL-5 cells does not affect IκBα degradation in response to CD40L (500 ng/mL).

The data presented here indicate that treatment of B-cell lymphoma cell lines with the EZH2 inhibitor, tazemetostat induces cell fate decisions; that B-cell maturation events are observed in both WT and mutant EZH2 NHL cell lines in response to tazemetostat; that EZH2 inhibition creates a dependency on B-cell activation signals; and that Tazemetostat inhibition of EZH2 induces anti proliferative effects, including B cell differentiation programs, in DLBCL cell lines irrespective of EZH2 mutational status and cell of origin.

The observation of synergistic effects of tazemetostat with other agents, including, for example, second therapeutic agents for the treatment of various cancers indicate that combination treatments with tazemetostat and such synergistic agents are useful treatment modalities for various cancers, including, e.g., cancers that are not sensitive to single-agent treatment modalities.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method for treating a germinal center-derived lymphoma in a subject in need thereof comprising administering to the subject a therapeutically effective amount of an EZH2 inhibitor and a CD40 agonist.

2. The method of claim 1, wherein the germinal center-derived lymphoma is an EZH2 wild type germinal center B-cell lymphoma.

3. The method of claim 1, wherein the CD40 agonist comprises CD40L, a CD40-binding fragment of CD40L, an agonistic CD40 antibody, an agonistic CD40 antibody fragment, CP870,893, SGN-40, a CD40 agonist peptide, or a small molecule.

4. The method of claim 1, wherein the EZH2 inhibitor is administered orally.

5. The method of claim 1, wherein the subject is a human being.

6. The method of claim 1, wherein the EZH2 inhibitor is of Formula (I):

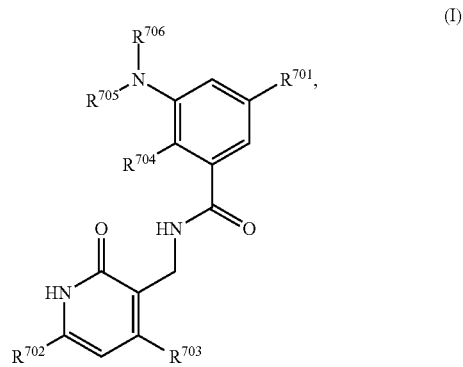

or a pharmaceutically acceptable salt thereof; wherein $R^{701}$ is H, F, $OR^{707}$, $NHR^{707}$, —(C≡C)—$(CH_2)_{n7}$—$R^{708}$, phenyl, 5- or 6-membered heteroaryl, $C_{3-8}$ cycloalkyl, or 4-7 membered heterocycloalkyl containing 1-3 heteroatoms, wherein the phenyl, 5- or 6-membered heteroaryl, $C_{3-8}$ cycloalkyl or 4-7 membered heterocycloalkyl each independently is optionally substituted with one or more groups selected from halo, $C_{1-3}$ alkyl, OH, O—$C_{1-6}$ alkyl, NH—$C_{1-6}$ alkyl, and, $C_{1-3}$ alkyl substituted with $C_{3-8}$ cycloalkyl or 4-7 membered heterocycloalkyl containing 1-3 heteroatoms, wherein each of the O—$C_{1-6}$ alkyl and NH—$C_{1-6}$ alkyl is optionally substituted with hydroxyl, O—$C_{1-3}$ alkyl or NH—$C_{1-3}$ alkyl, each of the O—$C_{1-3}$ alkyl and NH—$C_{1-3}$ alkyl being optionally further substituted with O—$C_{1-3}$ alkyl or NH—$C_{1-3}$ alkyl;

each of $R^{702}$ and $R^{703}$, independently is H, halo, $C_{1-4}$ alkyl, $C_{1-6}$ alkoxyl or $C_{6-10}$ aryloxy, each optionally substituted with one or more halo;

each of $R^{704}$ and $R^{705}$, independently is $C_{1-4}$ alkyl;

$R^{706}$ is cyclohexyl substituted by $N(C_{1-4}$ alkyl$)_2$ wherein one or both of the $C_{1-4}$ alkyl is optionally substituted with $C_{1-6}$ alkoxy; or $R^{706}$ is tetrahydropyranyl;

$R^{707}$ is $C_{1-4}$ alkyl optionally substituted with one or more groups selected from hydroxyl, $C_{1-4}$ alkoxy, amino, mono- or di-$C_{1-4}$ alkylamino, $C_{3-8}$ cycloalkyl, and 4-7 membered heterocycloalkyl containing 1-3 heteroatoms, wherein the $C_{3-8}$ cycloalkyl or 4-7 membered heterocycloalkyl each independently is further optionally substituted with $C_{1-3}$ alkyl;

$R^{708}$ is $C_{1-4}$ alkyl optionally substituted with one or more groups selected from OH, halo, and $C_{1-4}$ alkoxy, 4-7 membered heterocycloalkyl containing 1-3 heteroatoms, or O—$C_{1-6}$ alkyl, wherein the 4-7 membered heterocycloalkyl can be optionally further substituted with OH or $C_{1-6}$ alkyl; and $n_7$ is 0, 1 or 2.

7. The method of claim 1, wherein the EZH2 inhibitor is EPZ-6438 having the following formula:

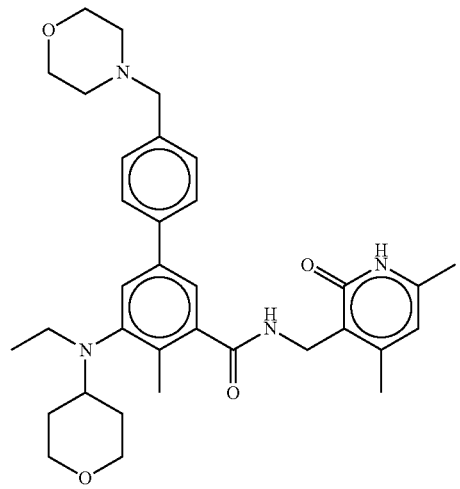

(EPZ-6438) or a pharmaceutically acceptable salt thereof.

8. The method of claim 7, wherein the EZH2 inhibitor is administered to the subject at a dose of about 100 mg to about 3,200 mg daily.

9. The method of claim 7, wherein the EZH2 inhibitor is administered to the subject at a dose of about 100 mg BID to about 1,600 mg BID.

10. The method of claim 7, wherein the EZH2 inhibitor is administered to the subject at a dose of about 100 mg BID, 200 mg BID, 400 mg BID, 800 mg BID, or about 1,600 mg BID.

11. The method of claim 1, wherein the EZH2 inhibitor is:

(A)

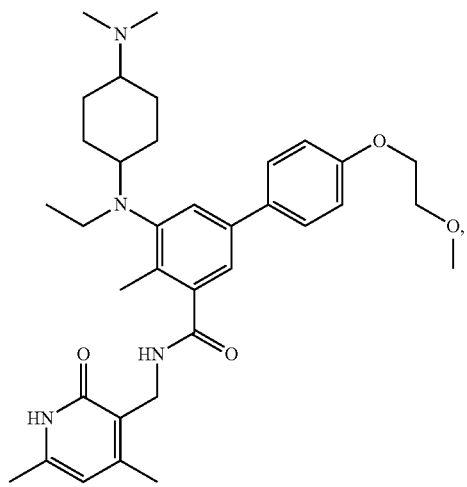

(B)

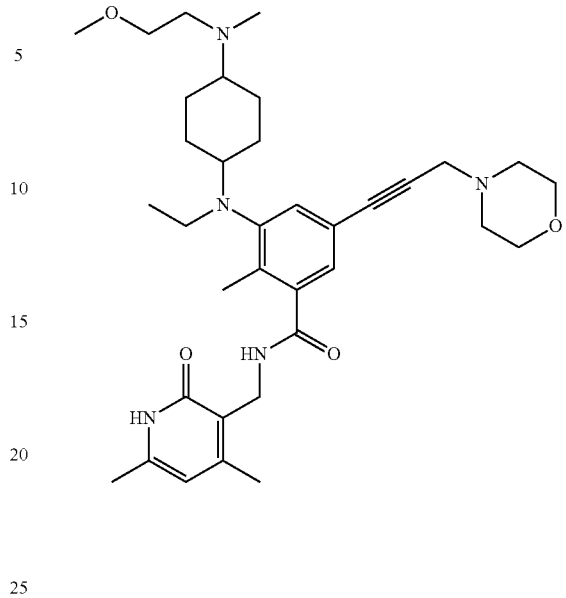

(C)

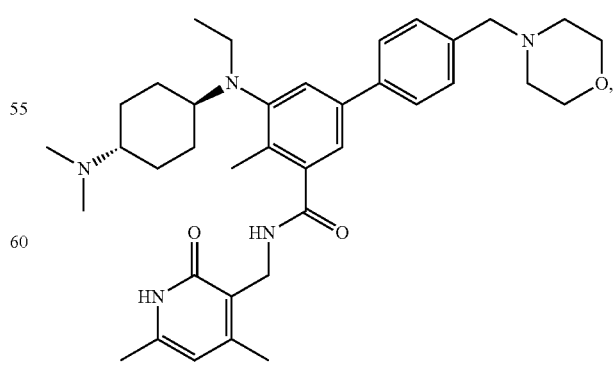

, or (D)

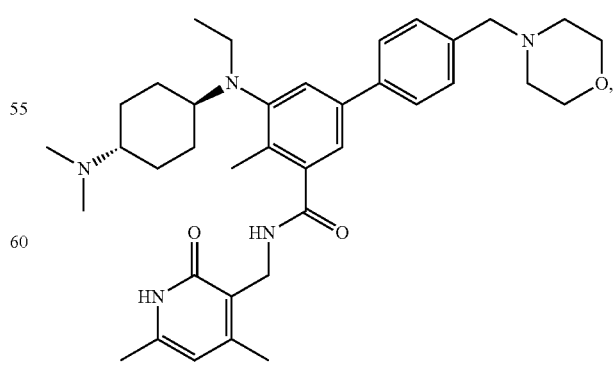

or a pharmaceutically acceptable salt thereof.

12. The method of claim 1, wherein the EZH2 inhibitor

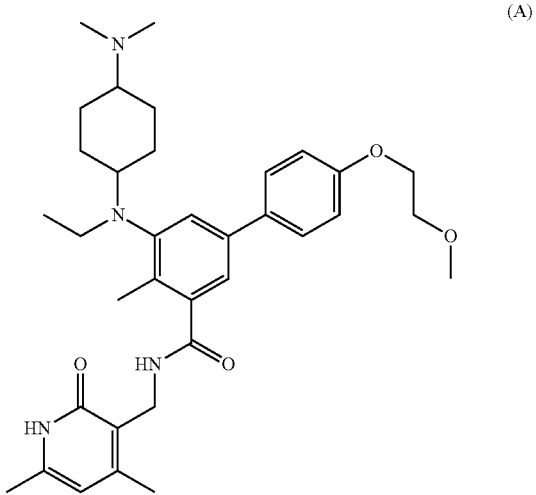

(A)

or a pharmaceutically acceptable salt thereof.

13. The method of claim 1, wherein the CD40 agonist is CD40L.

14. The method of claim 1, wherein the CD40 agonist comprises an anti-CD40 antibody or an anti-CD40 antibody fragment.

15. The method of claim 1, wherein the EZH2 inhibitor and the CD40 agonist are administered simultaneously or sequentially.

16. The method of claim 1, wherein the EZH2 inhibitor is administered prior to administration of the CD40 agonist.

17. The method of claim 1, wherein the CD40 agonist is administered prior to administration of the EZH2 inhibitor.

18. The method of claim 1, wherein the germinal center-derived lymphoma is diffuse large B-cell lymphoma, follicular lymphoma, Burkitt's lymphoma or Non-Hodgkin's Lymphoma of germinal center B-cell subtype.

19. The method of claim 6, wherein the CD40 agonist comprises CD40L, a CD40-binding fragment of CD40L, an agonistic CD40 antibody, an agonistic CD40 antibody fragment, CP870,893, SGN-40, a CD40 agonist peptide, or a small molecule.

20. The method of claim 6, wherein the CD40 agonist comprises an anti-CD40 antibody or an anti-CD40 antibody fragment.

21. The method of claim 6, wherein the CD40 agonist is CD40L.

22. The method of claim 21, wherein the germinal center-derived lymphoma is diffuse large B-cell lymphoma, follicular lymphoma, Burkitt's lymphoma or Non-Hodgkin's Lymphoma of germinal center B-cell subtype.

23. The method of claim 6, wherein the germinal center-derived lymphoma is diffuse large B-cell lymphoma, follicular lymphoma, Burkitt's lymphoma or Non-Hodgkin's Lymphoma of germinal center B-cell subtype.

24. The method of claim 7, wherein the CD40 agonist comprises CD40L, a CD40-binding fragment of CD40L, an agonistic CD40 antibody, an agonistic CD40 antibody fragment, CP870,893, SGN-40, a CD40 agonist peptide, or a small molecule.

25. The method of claim 7, wherein the CD40 agonist comprises an anti-CD40 antibody or an anti-CD40 antibody fragment.

26. The method of claim 7, wherein the CD40 agonist is CD40L.

27. The method of claim 26, wherein the germinal center-derived lymphoma is diffuse large B-cell lymphoma, follicular lymphoma, Burkitt's lymphoma or Non-Hodgkin's Lymphoma of germinal center B-cell subtype.

28. The method of claim 7, wherein the germinal center-derived lymphoma is diffuse large B-cell lymphoma, follicular lymphoma, Burkitt's lymphoma or Non-Hodgkin's Lymphoma of germinal center B-cell subtype.

29. The method of claim 7, wherein the germinal center-derived lymphoma is diffuse large B-cell lymphoma.

* * * * *